United States Patent
Kim et al.

(10) Patent No.: US 10,227,618 B2
(45) Date of Patent: Mar. 12, 2019

(54) MICROORGANISM PRODUCING LACTIC ACID AND METHOD FOR PRODUCING LACTIC ACID USING SAME

(71) Applicant: CJ Cheiljedang Corporation, Seoul (KR)

(72) Inventors: Seon Hye Kim, Gyeonggi-do (KR); Tae Hee Lee, Gyeonggi-do (KR); Young Lyeol Yang, Seoul (KR); Eun Bin Yang, Seoul (KR); Kyungsu Na, Gyeonggi-do (KR); Cheol Woong Ha, Gyeonggi-do (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/735,074

(22) PCT Filed: Jun. 10, 2016

(86) PCT No.: PCT/KR2016/006187
§ 371 (c)(1),
(2) Date: Dec. 8, 2017

(87) PCT Pub. No.: WO2016/200207
PCT Pub. Date: Dec. 15, 2016

(65) Prior Publication Data
US 2018/0320206 A1 Nov. 8, 2018

(30) Foreign Application Priority Data
Jun. 12, 2015 (KR) .................. 10-2015-0083658

(51) Int. Cl.
*C12N 9/90* (2006.01)
*C12P 7/56* (2006.01)
*C12N 1/14* (2006.01)
*C07K 14/395* (2006.01)
*C12N 15/81* (2006.01)

(52) U.S. Cl.
CPC .............. *C12P 7/56* (2013.01); *C07K 14/395* (2013.01); *C12N 15/81* (2013.01); *C12Y 101/01002* (2013.01); *C12Y 101/01028* (2013.01); *C12Y 401/01001* (2013.01)

(58) Field of Classification Search
CPC .................................. C12N 15/52; C12P 7/56
USPC ......................................................... 435/233
See application file for complete search history.

(56) References Cited

U.S. PATENT DOCUMENTS

| 9,617,570 B2* | 4/2017 | Lim .................. C12P 7/56 |
| 2007/0031950 A1 | 2/2007 | Winkler |
| 2015/0044740 A1 | 2/2015 | Kim et al. |

FOREIGN PATENT DOCUMENTS

| EP | 1975232 A1 | 10/2008 |
| JP | 2003-500062 A | 1/2003 |
| JP | 2013-21940 A | 2/2013 |
| KR | 10-1295369 B1 | 8/2013 |
| KR | 2015 0078989 A | 7/2015 |
| WO | WO 0242471 A2 | 5/2002 |
| WO | WO 2013/036764 A1 | 3/2013 |
| WO | WO 2015/057154 A2 | 4/2015 |

OTHER PUBLICATIONS

Boles et al. 1997. Characterization of a glucose-repressed pyruvate kinase (Pyk2p) in *Saccharomyces cerevisiae* that is catalytically insensitive to fructose-1,6-bisphosphate. *Journal of Bacteriology*, 179(9):2987-2993.
Cao et al. 2013. Fermentative succinate production: An emerging technology to replace the traditional petrochemical processes. *BioMed Research International*, vol. 2013, Article ID 723412, 12 pages.
Chypre et al. 2012. ATP-citrate lyase: A mini-review. *Biochemical and Biophysical Research Communications*, 422(2012)1-4.
Ishida et al. 2006. The effect of pyruvate decarboxylase gene knockout in *Saccharomyces cerevisiae* on L-Lactic acid production. *Bioscience, Biotechnology, and Biochemistry*, 70(5):1148-1153.
Lee et al. 2006. Development of reusable split URA3-marked knockout vectors for *Saccharomyces cerevisiae. J. Microbiol. Biotechnol.* 16(6):979-982.
Lian et al. 2015. Recent advances in biosynthesis of fatty acids derived products in *Saccharomyces cerevisiae* via enhanced supply of precursor metabolites. *J. Ind. Microbiol. Biotechnol.*, 42:437-451.
Moreira dos Santos et al. 2004. Manipulation of malic enzyme in *Saccharomyces cerevisiae* for increasing NADPH production capacity aerobically in different cellular compartments. *Metabolic Engineering*, 6(2004):352-363.
NCBI GenBank Accession No. EGA85775.1 dated Feb. 11, 2011, 2 pages.
NCBI Reference Sequence NP_011601.3 dated Feb. 18, 2015.
NCBI Reference Sequence NP_012896.1 dated Feb. 18, 2015.
NCBI Reference Sequence NP_013023.3 dated Feb. 18, 2015.
NCBI Reference Sequence NP_013235.1 dated Feb. 18, 2015.
NCBI Reference Sequence NP_014515.2 dated Feb. 18, 2015.
NCBI Reference Sequence NP_014992.3 dated Feb. 18, 2015.
NCBI Reference Sequence NP_0598798.1 dated Feb. 15, 2015.

(Continued)

*Primary Examiner* — Tekchand Saidha
(74) *Attorney, Agent, or Firm* — Knobbe Martens Olson & Bear LLP

(57) ABSTRACT

The present application relates to a microorganism of the genus *Saccharomyces* producing lactic acid and a method for preparing lactic acid using the same. More specifically, the present application relates to a microorganism of the genus *Saccharomyces* producing lactic acid, wherein the microorganism is modified to weaken or inactivate the activity of pyruvate decarboxylase (PDC) compared to its endogenous activity, to introduce the activity of ATP-citrate lyase (ACL), and to enhance pyruvate biosynthetic pathway compared to its endogenous biosynthetic pathway, and a method for producing lactic acid using the microorganism.

12 Claims, 1 Drawing Sheet
Specification includes a Sequence Listing.

(56) References Cited

OTHER PUBLICATIONS

NCBI Reference Sequence NP_001186225 dated Sep. 25, 2017.
NCBI Reference Sequence WP_003640741.1 dated Jun. 3, 2015.
Yin et al. 2000. Differential post-transcriptional regulation of yeast mRNAs in response to high and low glucose concentrations. *Molecular Microbiology*, 35(3):553-565.
International Search Report dated Oct. 6, 2016 for International Application No. PCT/KR2016/006187 filed Jun. 10, 2016, 8 pages.
Written Opinion dated Oct. 6, 2016 for International Application No. PCT/KR2016/006187 filed Jun. 10, 2016, 7 pages.
Supplementary European Search Report issued in European Patent Application No. 16807847.5, dated Sep. 27, 2018.
Office Action issued in Japanese Patent Application No. 2017-564531, dated Dec. 11, 2018.

\* cited by examiner

MICROORGANISM PRODUCING LACTIC ACID AND METHOD FOR PRODUCING LACTIC ACID USING SAME

CROSS-REFERENCE TO RELATED APPLICATIONS

This application is a U.S. National Phase Application of PCT International Application No. PCT/KR2016/006187, filed on Jun. 10, 2016, designating the United States of America, which is an International Application of and claims the benefit of priority to Korean Patent Application No. 10-2015-0083658, filed on Jun. 12, 2015.

SEQUENCE LISTING STATEMENT

The present application contains a Sequence Listing, which is being submitted via EFS-Web on even date herewith. The Sequence Listing is submitted in a file entitled "Sequence_Listing_HAN030-004APC.txt," which was created on Nov. 29, 2017, and is approximately 85 kb in size. This Sequence Listing is hereby incorporated by reference.

TECHNICAL FIELD

The present application relates to a microorganism of the genus *Saccharomyces* producing lactic acid and a method for producing lactic acid using the same.

BACKGROUND ART

Lactic acid has a wide range of applications in the industry including foods, medicines, cosmetics, etc. Recently, due to the use of lactic acid as a monomer for polylactic acid, the demand has significantly increased. Methods for producing lactic acid include a traditional chemical synthesis and a biological fermentation process, which has carbohydrates as substrates, and the latter has been favored recently.

Generally, in yeast-based lactic acid-producing microorganisms, lactate dehydrogenase (LDH) and pyruvate decarboxylase (PDC) compete for the use of pyruvate as a substrate. In this regard, it is necessary to minimize the functions of PDC for higher production of lactic acid (LA) by LDH for maximizing the production yield of pyruvate. In *Saccharomyces cerevisiae*, PDC is present in three different forms of isozymes, i.e., PDC1, PDC5, and PDC6. Therefore, for maximizing lactic acid production, a method for preparing a strain with a simultaneous triple-deletion of PDC1, PDC5, and PDC6 may be used. However, although the inactivation of the PDC activity may increase the yield of lactic acid, it also has disadvantages in that it reduces productivity and that strains cannot be grown smoothly (European Patent No. EP2041264), thus making it difficult to produce a desired amount of lactic acid. Additionally, yeasts, such as the genus *Saccharomyces*, cannot exactly predict whether a desired amount of lactic acid can be produced by a simple gene manipulation by various cell organelles and various organic systems, unlike in prokaryotes such as bacteria.

DISCLOSURE

Technical Problem

The present inventors have endeavored to develop a method for increasing both production yield and production amount of lactic acid while maintaining a smooth growth of lactic acid-producing microorganism, and as a result, have confirmed that enhancing the supply pathway of acetyl-CoA and the supply pathway from oxaloacetate (OAA) to pyruvate improved the amount of lactic acid production, thereby completing the present application.

Technical Solution

An object of the present application is to provide a microorganism of the genus *Saccharomyces* producing lactic acid.

Another object of the present application is to provide a method for producing lactic acid using the microorganism.

Advantageous Effects

The modified lactic acid-producing strain of the present application, where PDC activity is inactivated, the foreign ACL activity is introduced, and the biosynthetic pathway for pyruvate is enhanced, has excellent lactic acid fermentation yield and productivity compared to the conventional strains, by minimizing the fermentation of producing the alcohol and blocking of the lactic acid decomposition pathway. Therefore, the growth of the lactic acid-producing strain has been increased, and the modified lactic acid-producing strain of the present application can be widely used for improving the productivity of various products prepared using lactic acid as a raw material. The thus-produced lactic acid can be provided as a raw material for various kinds of products.

BEST MODE FOR CARRYING OUT INVENTION

Figure 1:
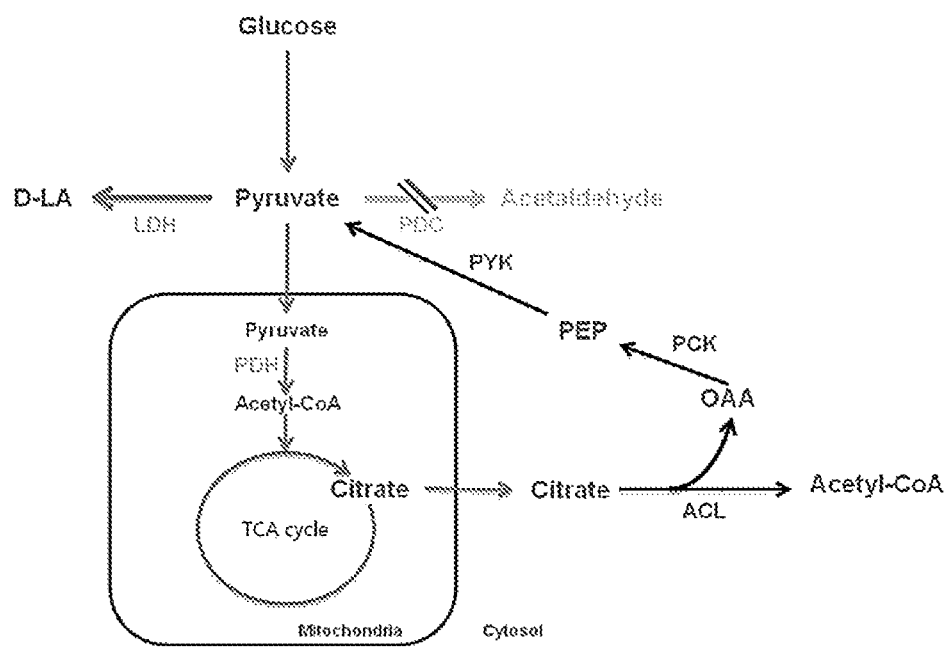
FIG. 1 is a pathway for enhancing the biosynthesis of pyruvate via an overexpression of PEP carboxykinase (PCK 1, EC 4.1.1.49) and pyruvate kinase (PYK 2, EC 2.7.1.40) present in a yeast microorganism, and shows a schematic diagram illustrating a strategy for improving lactic acid productivity by the introduction of foreign ACL and the enhancement of PCK and PYK pathways of the present application.

To achieve the above objects, in an aspect, the present application provides a microorganism of the genus *Saccharomyces* producing lactic acid, in which the microorganism is modified to inactivate the activity of pyruvate decarboxylase (PDC) compared to its endogenous activity, to introduce the activity of ATP-citrate lyase (ACL), and to enhance pyruvate biosynthetic pathway compared to its endogenous biosynthetic pathway.

The microorganism of the genus *Saccharomyces* producing lactic acid may be a microorganism, in which lactic acid fermentation yield is increased and/or growth of the body of a microorganism of the genus *Saccharomyces* is increased (the increase of the growth of the microorganism with productivity) and/or lactic acid productivity is increased, compared to the unmodified strains, wherein ACL activity is not introduced and/or the biosynthetic pathway of pyruvate is not enhanced relative to the endogenous biosynthetic pathway.

As used herein, the term "lactic acid (LA)" refers to an organic acid represented by $C_2H_4OHCOOH$. When such lactic acid is produced by a chemical synthesis, lactic acid is produced in the form of a racemic mixture in which D-type lactic acid and L-type lactic acid are mixed in a 50/50 ratio, and it is impossible to control the composition ratio. Therefore, when polylactic acid is prepared, the lactic acid becomes an amorphous polymer with a low melting point, and thus there are many limitations in developing its use. In contrast, when lactic acid is produced by a biological fermentation method using a microorganism, D-type lactic acid and L-type lactic acid can be selectively produced according to the bacteria being used or the lactate dehydrogenase (LDH) being introduced therein.

As used herein, the term "a microorganism producing lactic acid" refers to a microorganism strain, which produces lactic acid productivity, in the present application, can convert sugar into lactic acid, and for example, may include any yeast microorganism without any limitation as long as it includes lactic acid synthesis pathway and acetyl-CoA synthesis pathway of the present application.

According to their shapes, yeast microorganisms may be classified into the genus *Saccharomyces*, the genus *Pichia*, the genus *Candida*, and the genus *Saccharomycopsis*, and specifically, the microorganism of the genus *Saccharomyces* including various species may be used in the present application as long as the microorganism can produce lactic acid. Specifically, the *Saccharomyces* sp. microorganism may be one selected from the group consisting of *Saccharomyces bayanus*, *Saccharomyces boulardii*, *Saccharomyces bulderi*, *Saccharomyces cariocanus*, *Saccharomyces cariocus*, *Saccharomyces cerevisiae*, *Saccharomyces chevaliers*, *Saccharomyces dairenensis*, *Saccharomyces ellipsoideus*, *Saccharomyces eubayanus*, *Saccharomyces exiguus*, *Saccharomyces florentinus*, *Saccharomyces kluyveri*, *Saccharomyces martiniae*, *Saccharomyces monacensis*, *Saccharomyces norbensis*, *Saccharomyces paradoxus*, *Saccharomyces pastorianus*, *Saccharomyces spencerorum*, *Saccharomyces turicensis*, *Saccharomyces unisporus*, *Saccharomyces uvarum*, and *Saccharomyces zonatus*, and more specifically *Saccharomyces cerevisiae*.

The microorganism of the genus *Saccharomyces* producing lactic acid of the present application may be a microorganism, wherein the microorganism is modified to inactivate the activity of pyruvate decarboxylase (PDC) compared to its endogenous activity, to introduce the activity of ATP-citrate lyase, and to enhance pyruvate biosynthetic pathway compared to its endogenous biosynthetic pathway.

Specifically, the *Saccharomyces* sp. microorganism producing lactic acid may be a microorganism, wherein the microorganisms is modified (i) to inactivate the activity of pyruvate decarboxylase (PDC) compared to its endogenous activity, (ii) to introduce the activity of ATP-citrate lyase, and (iii) to enhance pyruvate biosynthetic pathway compared to its endogenous biosynthetic pathway, and is further modified (iv) to introduce the activity of lactate dehydrogenase (LDH), (v) to weaken or inactivate the activity of alcohol dehydrogenase 1 compared to its endogenous activity, (vi) to weaken or inactivate the activity of pyruvate decarboxylase 1 compared to its endogenous activity, and/or (vii) to weaken or inactivate the activity of D-lactate dehydrogenase 1 compared to its endogenous activity.

Additionally, the microorganism of the present application may be further modified (i) to inactivate the activity of alcohol dehydrogenase 1 (ADH1) compared to its endogenous activity; (ii) to inactivate the activity of pyruvate decarboxylase 1 (PDC1) compared to its endogenous activity; and (iii) to inactivate the activity of D-lactate dehydrogenase 1 (DLD1) compared to its endogenous activity.

As used herein, the term "pyruvate decarboxylase (PDC)", which may be used interchangeably with an enzyme that catalyzes the decarboxylation of pyruvate, refers to an enzyme that converts pyruvate into acetaldehyde and carbon dioxide ($CO_2$). Pyruvate decarboxylase is an enzyme involved in a fermentation process in an anaerobic condition occurring in yeasts, in particular in a *Saccharomyces* sp., and it is an enzyme that produces ethanol by fermentation. Generally, the PDC in a *Saccharomyces* sp. is present in three different forms of isozymes, i.e., PDC1, PDC5, and PDC6. The protein and gene sequences of the PDC may be obtained from a known database such as GenBank of NCBI, but is not limited thereto. Specifically, regarding the enzyme, PDC1 may be a protein represented by an amino acid sequence of SEQ ID NO: 39, PDC5 may be a protein represented by an amino acid sequence of SEQ ID NO: 41, and PDC 6 may be a protein represented by an amino acid sequence of SEQ ID NO: 43, but any amino acid sequence having the activity of PDC can be included without limitation. Additionally, the genes encoding PDC1, PDC5, and PDC6 may be specifically represented by the nucleotide sequences of, for example, SEQ ID NOS: 40, 42, and 44, respectively, but any nucleotide sequence that can encode the enzyme may be included without limitation.

As used herein, the term "ATP-citrate lyase (ACL, EC 2.3.3.8)" refers to an enzyme which converts citrate into oxaloacetate (OAA) and acetyl-CoA and is known to be present in higher organisms and some yeasts (ATP-citrate lyase: A mini-review, *Biochemical and Biophysical Research Communications*, 422, (2012), 1-2).

The reaction scheme is shown below:

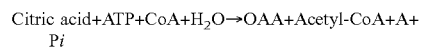

Citric acid+ATP+CoA+$H_2O$→OAA+Acetyl-CoA+A+Pi

Acetyl-CoA is an essential enzyme for the growth of microorganisms and its importance has been highlighted in various references recently. As a representative example, there was a report on a study for improving productivity in a eukaryotic organism capable of producing 1,3-butanediol (1,3-BDO) by providing cytosol acetyl-coA through a non-natural pathway (International Patent Publication No. WO 2013/036764).

In this regard, it is made possible to provide the acetyl-CoA, which is essential for the growth of a strain in which the activity of PDC is weakened or removed, by the introduction of exogenous ACL, thereby enabling the microorganism to grow in a manner independent of PDC activity. The protein- and gene sequences may be obtained from a known database, e.g., GenBank of NCBI, etc., but is not limited thereto. Specifically, ATP-citrate lyase may have an amino acid sequence of SEQ ID NO: 29, but any protein sequence having the enzyme activity may be included without limitation. Additionally, the gene encoding the ACL may be specifically represented by the nucleotide sequence of SEQ ID NO: 30, but any sequence encoding the enzyme may be included without limitation.

As used herein, the term "pyruvate biosynthesis pathway", which refers to a biosynthetic pathway that can provide pyruvate in a microorganism of the genus *Saccha-*

Figure 2:
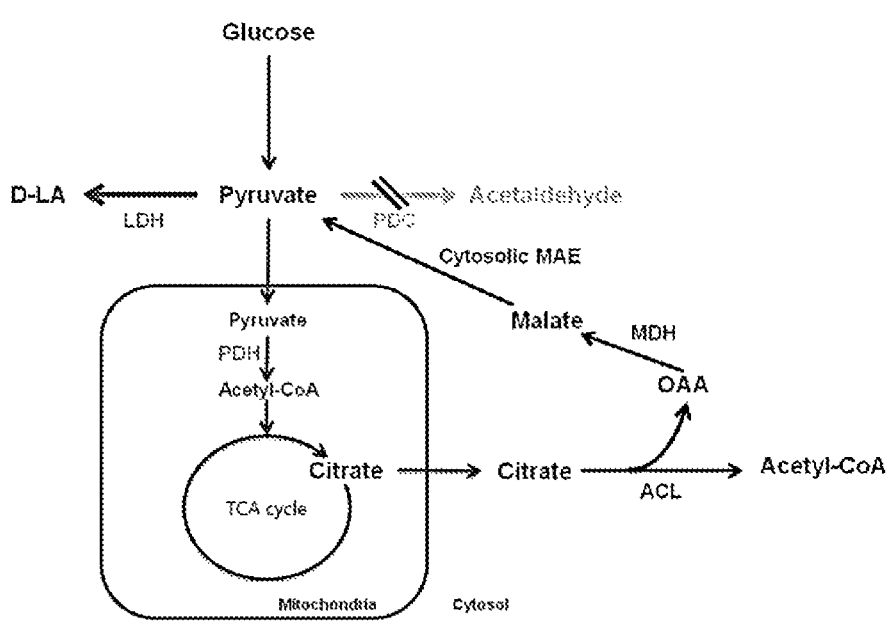
FIG. 2 is a pathway for enhancing the biosynthesis of pyruvate by the enhancement of malate dehydrogenase 2 (MDH2, EC 1.1.1.37) and cytosolic malic enzyme 1 (MAE1, EC 1.1.1.38) present in a yeast microorganism, and shows a schematic diagram illustrating a strategy for improving lactic acid productivity by the introduction of foreign ACL and through the MDH and cytosolic MAE pathways of the present application.

*romyces*, may be a supply route from OAA to pyruvate. Specific examples are shown in FIGS. 1 and 2.

In an exemplary embodiment, the pyruvate biosynthesis pathway may be performed by modifying the activities of phosphoenolpyruvate carboxykinase 1 (PCK1) or pyruvate kinase 2 (PYK2) or both enzymes to enhance their activities compared to their endogenous activities.

Alternatively, the pyruvate biosynthesis pathway may be performed by modifying the activities of malate dehydrogenase 2 (MDH2) or cytosolic malic enzyme 1 (cytosolic MAE1) or both enzymes to enhance their activities compared to their endogenous activities.

As used herein, the term "phosphoenolpyruvate carboxykinase 1 (PCK1)" refers to an enzyme that catalyzes the conversion of OAA into phosphoenolpyruvate (PEP). PCK1 is an enzyme necessary for gluconeogenesis to convert OAA into PEP in a yeast microorganism and its expression is known to be inhibited in the presence of glucose (Differential post-transcriptional regulation of yeast mRNAs in response to high and low glucose concentrations. *Mol Microbiol* 35 (3): 553-65 (2000)).

As used herein, the term "pyruvate kinase 2 (PYK2)" refers to an enzyme, which catalyzes the production of pyruvate and ATP by delivering a phosphate group from PEP to ADP. PYK2 is the enzyme in the final step of glycolysis in a yeast microorganism and its expression is also known to be inhibited in the presence of glucose (Characterization of a glucose-repressed pyruvate kinase (Pyk2p) in *Saccharomyces cerevisiae* that is catalytically insensitive to fructose-1,6-bisphosphate, *J Bacteriol*. 1997 May; 179 (9): 2987-93).

Each of the protein and gene sequences may be obtained from a known database, e.g., GenBank of NCBI, etc., but is not limited thereto. The PCK1 may have an amino acid sequence of SEQ ID NO: 31, but any protein sequence having the enzyme activity may be included without limitation. Additionally, the gene encoding the PCK1 may be specifically represented by the nucleotide sequence of SEQ ID NO: 32, but any sequence encoding the enzyme may be included without limitation. The PYK2 may have an amino acid sequence of SEQ ID NO: 33, but any protein sequence having the enzyme activity may be included without limitation. Additionally, as a specific example, the gene encoding the PYK2 may be represented by the nucleotide sequence of SEQ ID NO: 34, but any sequence that can encode the enzyme may be included without limitation.

As used herein, the term "malate dehydrogenase 2 (MDH2)" refers to a reversible enzyme which converts OAA into malate. The MDH2 is an enzyme, which is originally located in the cytosol.

As used herein, the term "cytosolic malic enzyme 1 (MAE1)" refers to an enzyme which was modified to be located in the cytosol by removing the mitochondrial targeting sequence from the MAE1, which is an enzyme to substitute malate with pyruvate. The MAE1 enzyme is a protein originally located in the mitochondria, and it converts malate, which is an intermediate material in the tricarboxylic acid (TCA) cycle, into pyruvate in the mitochondria (*Metabolic Engineering*, 6 (2004), 352-363). Each of the protein and gene sequences may be obtained from a known database, e.g., GenBank of NCBI, etc., but is not limited thereto. The MDH2 may have an amino acid sequence of SEQ ID NO: 35, but any protein sequence having the enzyme activity may be included without limitation. Additionally, as a specific example, the gene encoding the MDH2 may be represented by the nucleotide sequence of SEQ ID NO: 36, but any sequence which can encode the enzyme may be included without limitation. The MAE1 may have an amino acid sequence of SEQ ID NO: 37, but any protein sequence having the enzyme activity may be included without limitation. Additionally, for the MAE1 to be present in the cytosol, the MAE1 may have a sequence of the amino acid sequence of SEQ ID NO: 37 in which the amino acid residues at positions from the beginning to position 30 are removed (i.e., a sequence from which the amino acid sequence of SEQ ID NO: 51, a mitochondrial targeting sequence, is removed), and the sequence is represented by SEQ ID NO: 52. Additionally, in a specific example, the gene encoding the MAE1 may be represented by the nucleotide sequence of SEQ ID NO: 38, but any sequence that can encode the enzyme may be included without limitation.

As used herein, the term "lactate dehydrogenase (LDH)" refers to an enzyme, which can catalyze the conversion of lactate to pyruvate and back, and the protein and gene sequences may be obtained from a known database, e.g., GenBank of NCBI, etc., but is not limited thereto. The LDH may have an amino acid sequence of SEQ ID NO: 49, but any protein sequence having the enzyme activity may be included without limitation. Additionally, the gene encoding the LDH may be represented by the nucleotide sequence of SEQ ID NO: 50, but any sequence which can encode the enzyme may be included without limitation.

Each of the enzymes described above may include without limitation, in addition to the amino acid sequences represented by SEQ ID NOS, any amino acid sequence, which has a homology of 70% or higher, specifically 80% or higher, more specifically 90% or higher, even more specifically 95% or higher, yet even more specifically 98% or higher, and yet even still more specifically 99% or higher, to each of the above-listed amino acid sequences, as long as the enzyme exhibits practically the same or corresponding effect to each of the enzymes. Additionally, it is obvious that any modified enzyme, which has the homology described above and has the effect corresponding to each enzyme, can belong to the scope of the present application, although the enzyme may have an amino acid sequence with a partial deletion, modification, substitution, or addition.

Additionally, the genes encoding each of the enzymes may also include without limitation, in addition to the nucleotide sequences represented by SEQ ID NOS, any gene sequence encoding the enzymes, which has a homology of 80% or higher, specifically 90% or higher, more specifically 95% or higher, even more specifically 98% or higher, and yet even more specifically 99% or higher, to each of the above-listed nucleotide sequences, as long as the sequence encodes an enzyme which has substantially the same or corresponding effect to each of the enzymes. Additionally, it is obvious that any nucleotide sequence, which has the above homology can belong to the scope of the present application, although the sequence may have a partial deletion, modification, substitution, or addition therein.

As used herein, the term "homology" refers to a percentage of identity between two polynucleotide or polypeptide moieties. Sequence correspondence from one moiety to another may be determined by a known technique in the art. For example, homology may be determined by directly aligning the sequence information (e.g., parameters such as score, identity, and similarity) on two polynucleotide molecules or two polypeptide molecules using a computer program (e.g., BLAST 2.0) that is readily available and capable of aligning sequence information. Additionally, homology may be determined by hybridizing the polynucleotides under the condition for forming a stable double-strand in the homologous regions and digesting the hybridized strand by a single-strand-specific nuclease to determine the size of digested fragments.

As used herein, the term "endogenous activity" refers to a condition, where a microorganism has a natural state of enzymes or an activation level of enzymes prior to the modification of the corresponding enzymes.

As used herein, the term "the activity of an enzyme is modified for inactivation compared to its endogenous activity" refers to that a gene encoding an enzyme is not expressed at all compared to that of the native strain or a strain before modification, or even when the gene is expressed, there is no activity or the activity is reduced.

The above reduction is a concept, which includes a case where the activity of an enzyme itself is reduced due to a modification of the gene encoding the enzyme, etc., compared to that of the endogenous activity originally possessed by a microorganism, a case where the overall level of enzyme activity within a cell is lower compared to that of the wild-type strain or the strain before modification, and also a combination thereof.

The inactivation of an enzyme may be achieved by various methods known in the art. Examples of the methods may include a method to substitute the gene encoding the enzyme on the chromosome with a gene mutated to reduce the enzymatic activity, including the case where the enzyme activity is removed; a method of introducing a modification in the expression regulatory sequence of the gene encoding the enzyme on the chromosome; a method of substituting the expression regulatory sequence of the gene encoding the enzyme with a sequence having weak or no activity; a method of deleting the entirety or a part of the gene encoding the enzyme on the chromosome; a method of introducing an antisense oligonucleotide (e.g., antisense RNA), which binds complementary to a transcript of the gene on the chromosome, thereby inhibiting the translation from the mRNA into the enzyme; a method of artificially incorporating a complementary sequence to the SD sequence into the upstream of the SD sequence of the gene encoding the enzyme, forming a secondary structure, thereby making the attachment of ribosome thereto impossible; a method of incorporating a promoter to the 3' terminus of the open reading frame (ORF) to induce a reverse transcription (reverse transcription engineering (RTE)), etc., and also a combination thereof, but are not limited thereto.

Specifically, the method of deleting the entirety or a part of a gene encoding an enzyme may be performed by substituting the polynucleotide encoding the endogenous target protein within the chromosome with a polynucleotide or marker gene having a partial deletion in the nucleic acid sequence using a vector for chromosomal insertion within a strain. In an exemplary embodiment of the method of deleting a part or the entirety of a gene, a method for deleting a gene by homologous recombination may be used.

As used herein, the term "a part" may vary depending on the kinds of polynucleotides, and it may specifically refer to 1 to 300, more specifically 1 to 100, and even more specifically 1 to 50, but is not particularly limited thereto.

As used herein, the term "homologous recombination" refers to a genetic recombination that occurs via crossover at genetic chain loci having a mutual homology.

Specifically, the expression regulatory sequence may be modified by inducing a modification of the expression regulatory sequence by a deletion, an insertion, a non-conservative or conservative substitution, or a combination thereof in the nucleic acid sequence of the expression regulatory sequence; or by substituting with a weaker promoter, etc. The expression regulatory sequence may include a promoter, an operator sequence, a sequence encoding a ribosome-binding region, and sequences controlling the termination of transcription and translation.

Furthermore, the gene sequence on the chromosome may be modified by inducing a modification in the sequence by a deletion, an insertion, a non-conservative or conservative substitution, or a combination thereof in the gene sequence for reducing the enzyme activity; or by substituting with a gene sequence which was improved to have a weaker activity or a gene sequence which was improved to have no activity.

As used herein, the term "enhancement of activity compared to its endogenous activity" refers to increasing the intracellular activity of a protein (or enzyme) in a microorganism by modifying the protein to improve the intracellular activity compared to the activity of the protein possessed in its natural state. The "enhancement" may include the drawing of a higher effect than the original function due to the increase in the activity of the protein (or enzyme) itself, and it may be performed by at least one method selected from the group consisting of a method of increasing the copy number of a polynucleotide encoding the protein (or enzyme), a method of introducing a modification in the regulatory sequence of a gene encoding the protein (or enzyme), a method of substituting the regulatory sequence of a gene encoding the protein (or enzyme) on the chromosome with a sequence having strong activity, a method of substituting the gene encoding the protein (or enzyme) with a mutated gene to increase the activity of the protein (or enzyme), and a method of introducing a modification in the gene encoding the protein (or enzyme) on the chromosome to enhance the activity of the protein (or enzyme), but any known method which can enhance the activity of the protein (or enzyme) compared to its endogenous activity or enhance the introduced activity may be included without limitation.

As used herein, the term "introduction of the activity of a protein (or enzyme)" refers to providing an activity of a particular protein (or enzyme) to a microorganism, which does not have the activity of the particular protein (or enzyme); or increasing the intracellular activity of a particular protein (or enzyme) in a microorganism, which does not have the activity of the particular protein (or enzyme) by modifying the microorganism to further improve the intracellular activity of the protein (or enzyme) after providing the activity of the particular protein (or enzyme) to the microorganism.

The "introduction of the activity of a protein (or enzyme)" may be performed in various methods known in the art, for example: a method of inserting a polynucleotide including a nucleotide sequence encoding the protein (or enzyme) into the chromosome; a method of increasing the copy number of a polynucleotide by a method such as introducing the polynucleotide to a microorganism via an introduction into a vector system; a method of introducing a promoter capable of exhibiting improved activity or introducing the protein (or enzyme) with a modification in the promoter, into an upstream region of the nucleotide sequence encoding the protein (or enzyme); a method of introducing a nucleotide variant sequence encoding the protein (or enzyme); etc., but any known method that can introduce the activity of a protein (or enzyme) may be included without limitation.

In the above, the increase of copy number of a polynucleotide may be performed in a form in which the polynucleotide is operably linked to a vector, or by inserting the polynucleotide into the chromosome of a host cell, although the method is not particularly limited thereto. Specifically, the increase of copy number of a polynucleotide may be performed by introducing a vector, which can replicate and function regardless of a host cell and the polynucleotide encoding the protein of the present application is operably linked thereto; or may be performed by introducing a vector, which can insert the polynucleotide into the chromosome of a host cell and the polynucleotide is operably linked thereto, into a host cell.

The vector is a DNA construct including the sequence of a polynucleotide encoding a target peptide, which is operably linked to an appropriate regulatory sequence to enable the expression of the target peptide in a host cell. The regulatory sequence includes a promoter capable of initiating transcription, any operator sequence for the regulation of the transcription, a sequence encoding an appropriate mRNA ribosome-binding domain, and a sequence regulating the termination of transcription and translation. The vector, after being transformed into an appropriate host cell, may be replicated or function regardless of the host genome, or may be integrated into the host genome itself.

For the yeast expression vector, both an integrative yeast plasmid (YIp) and an extrachromosomal plasmid vector may be used. The extrachromosomal plasmid vector may include episomal yeast plasmid (YEp), replicative yeast plasmid (YRp), and yeast centromer plasmid (YCp). Additionally, artificial yeast chromosomes (YACs) may be also used as expression vectors according to the present application. For example, the vectors to be used in the present application may include pESC-HIS, pESC-LEU, pESC-TRP, pESC-URA. Gateway pYES-DEST52, pAO815, pGAPZ A, pGAPZ B, pGAPZ C, pGAPα A, pGAPα B, pGAPα C, pPIC3.5K, pPIC6 A, pPIC6 B, pPIC6 C, pPIC6α A, pPIC6α B, pPIC6α C, pPIC9K, pYC2/CT, pYD1 Yeast Display Vector, pYES2, pYES2/CT, pYES2/NT A, pYES2/NT B, pYES2/NT C, pYES2/CT, pYES2.1, pYES-DEST52, pTEF1/Zeo, pFLD1, *Pichia*Pink™, p427-TEF, p417-CYC, pGAL-MF, p427-TEF, p417-CYC, PTEF-MF, pBY011, pSGP47, pSGP46, pSGP36, pSGP40, ZM552, pAG303GAL-ccdB, pAG414GAL-ccdB, pAS404, pBridge, pGAD-GH, pGAD T7, pGBK T7, pHIS-2, pOBD2, pRS408, pRS410, pRS418, pRS420, pRS428, yeast micron A form, pRS403, pRS404, pRS405, pRS406, pYJ403, pYJ404, pYJ405, and pYJ406, but are not limited thereto.

More specifically, the yeast vector may be a yeast replication plasmid including replication origin (ori) and an antibiotic resistance cassette which can be proliferated and selected in *E. coli*. Generally, expression vectors may include an expression construct of promoter-gene-transcription termination sequence.

For example, when the host cells is a yeast, the promoters that can be used in the expression construct may include TEF1 promoter, TEF2 promoter, GAL10 promoter, GAL1 promoter, ADH1 promoter, ADH2 promoter, PHO5 promoter, GAL1-10 promoter, TDH3 promoter (GPD promoter), TDH2 promoter, TDH1 promoter, PGK1 promoter, PYK2 promoter, ENO1 promoter, ENO2 promoter, and TPI1 promoter, but are not limited thereto.

The transcription termination sequences that can be used in the expression construct may include ADH1 terminator, CYC1 terminator, GAL10 terminator, PGK1 terminator, PHO5 terminator, ENO1 terminator, ENO2 terminator, and TPI1 terminator, but are not limited thereto.

Additionally, the polynucleotide encoding the endogenous target protein may be replaced with a modified polynucleotide within the chromosome by a vector for the insertion of chromosome within the host cell. Alternatively, the polynucleotide encoding a foreign target protein to be introduced into the chromosome may be replaced with a modified polynucleotide. The insertion of the polynucleotide into the chromosome may be performed using any known method in the art, for example, by homologous recombination. Since the vector of the present application can be inserted into the chromosome via homologous recombination, a selection marker for confirmation of the insertion into the chromosome may be further included. The selection marker is used for the selection of a transformed cell, i.e., to confirm whether the target polynucleotide has been inserted, and markers capable of providing selectable phenotypes such as drug resistance, nutrient requirement, resistance to cytotoxic agents, and expression of surface proteins may be used. Under the circumstances treated with selective agents, only the cells capable of expressing the selection markers can survive or express other phenotypic traits, and thus the transformed cells can be selected.

As used herein, the term "transformation" refers to a process of introducing a vector including a polynucleotide encoding a target protein into a host cell, thereby enabling the expression of the polynucleotide encoded by the protein in the host cell. For the transformed polynucleotide, it does not matter whether it is inserted into the chromosome of a host cell and located therein or located outside the chromosome, as long as it can be expressed in the host cell. Additionally, the polynucleotide includes DNA and RNA, which encode the target protein. The polynucleotide may be inserted in any form as long as it can be introduced into a host cell and expressed therein. For example, the polynucleotide may be introduced into a host cell in the form of an expression cassette, which is a gene construct including all essential elements required for self-expression. The expression cassette may conventionally include a promoter operably linked to the polynucleotide, a transcription termination signal, a ribosome-binding domain, and a translation termination signal. The expression cassette may be in the form of an expression vector capable of self-replication. Additionally, the polynucleotide may be introduced into a host cell as it is and operably linked to a sequence essential for its expression in the host cell.

Additionally, as used herein, the term "operably linked" refers to a functional connection between a promoter sequence, which initiates and mediates the transcription of the polynucleotide encoding the target protein of the present application, and the above target gene sequence.

The method of transforming a vector of the present application may include any method which can introduce nucleic acids into a cell, and the transformation may be performed by selecting an appropriate technique as known in the art according to the host cell. For example, the method may include electroporation, calcium phosphate (CaPO$_4$) precipitation, calcium chloride (CaCl$_2$) precipitation, microinjection, a polyethylene glycol (PEG) method, a DEAE-dextran method, a cationic liposome calcium, and a lithium acetate/DMSO method, etc., but are not limited thereto.

Specifically, the host cell to be used should have high efficiency of DNA introduction and high expression efficiency of the introduced DNA, and for the purpose of the present application, the host cell may be a microorganism of the genus *Saccharomyces*.

Then, the introduction of a modification in the expression regulatory sequence for increasing the expression of a polynucleotide, although not particularly limited thereto, may be performed by inducing modification in the nucleic acid sequence via deletion, insertion, conservative substitution or non-conservative substitution, or a combination thereof in order to further enhance the activity of the expression regulatory sequence; or by replacing the polynucleotide sequence with a nucleic acid sequence with enhanced activity. The expression regulatory sequence, although not particularly limited thereto, may include a promoter, an operator sequence, a sequence encoding a ribosome-binding domain, and a sequence for regulating the termination of transcription and translation, etc.

A strong exogenous promoter, instead of the original promoter, may be linked to the upstream region of the expression unit of the polynucleotide.

Generally, the introduction or enhancement of the activity of a protein may increase the activity or concentration of the corresponding protein relative to the activity or concentration of a wild-type protein or in a microorganism strain from at least 10%, 25%, 50%, 75%, 100%, 150%, 200%, 300%, 400%, or 500%, to a maximum of 1000% or 2000%.

In another aspect, the present application provides a method for producing lactic acid including a) culturing a novel microorganism of the genus *Saccharomyces* producing lactic acid, wherein the microorganism is modified to inactivate the activity of pyruvate decarboxylase (PDC) compared to its endogenous activity, to introduce the activity of ATP-citrate lyase (ACL), and to enhance pyruvate biosynthetic pathway compared to its endogenous biosynthetic pathway in a medium; and b) recovering lactic acid from the cultured microorganism and the culture.

The microorganism of the genus *Saccharomyces* producing lactic acid is the same as described above.

As used herein, the term "culturing" refers to growing a microorganism in an appropriately artificially adjusted environment. In the present application, the culturing using the microorganism of the genus *Saccharomyces* may be performed by an appropriate method well known in the art. Specifically, the culturing may be performed continuously in a batch process, a fed batch, or a repeated fed batch process, but is not limited thereto.

The media used for culturing the microorganism of the present application and other culture conditions are not particularly limited but any medium used for the conventional culturing of the microorganism of the genus *Saccharomyces* may be used. Specifically, the microorganism of the present application may be cultured in a conventional medium containing appropriate carbon sources, nitrogen sources, phosphorous sources, inorganic compounds, amino acids and/or vitamins, etc., in an aerobic condition while adjusting temperature, pH, etc.

As an example of the carbon sources, sucrose or glucose may be used, and molasses containing a large amount of sucrose may also be used as a carbon source, and an appropriate amount of other various kinds of carbon sources may be used.

Examples of the nitrogen sources may include organic nitrogen sources such as peptone, yeast extract, meat gravy, malt extract, corn steep liquor, and soybean flour; and inorganic nitrogen sources such as urea, ammonium sulfate, ammonium chloride, ammonium phosphate, ammonium carbonate, and ammonium nitrate. These nitrogen sources may be used alone or in combination. In the above medium, potassium dihydrogen phosphate, dipotassium hydrogen phosphate, and corresponding sodium-containing salts may be contained as phosphorus sources. Additionally, metal salts, such as magnesium sulfate or iron sulfate, may be contained. Furthermore, amino acids, vitamins, and appropriate precursors may be contained. These media or precursors may be added in a batch culture process or a continuous culture process to the culture.

During the period of the culture, the pH of a culture may be adjusted by adding a compound such as ammonium hydroxide, potassium hydroxide, ammonia, phosphoric acid, and sulfuric acid to the culture in an appropriate manner. Additionally, during the period of the culture, an antifoaming agent, such as fatty acid polyglycol ester, may be added to prevent foam generation. Additionally, for maintaining the aerobic state of the culture, oxygen or an oxygen-containing gas may be injected into the culture, and for maintaining the anaerobic and microaerophillic states of the culture, nitrogen, hydrogen, or carbon dioxide gas may be injected without the injection of an air.

The culture temperature may normally be from 20° C. to 40° C., specifically, from 25° C. to 35° C., and more specifically 30° C., but may vary without limitation according to the desired purposes. Additionally, the culturing may be continued until desired amount of product can be obtained, and specifically for 10 hours to 100 hours, but is not limited thereto.

The method of producing lactic acid of the present application may include recovering lactic acid from the cultured microorganism or the culture. The method of recovering the lactic acid from the microorganism or the culture may be performed using the appropriate method known in the art, e.g., centrifugation, filtration, anion exchange chromatography, crystallization, HPLC, etc., but is not limited thereto.

The recovering may include a purification process.

Modes for Carrying out Invention

Hereinbelow, the present application will be described in detail with accompanying exemplary embodiments. However, the exemplary embodiments disclosed herein are only for illustrative purposes and should not be construed as limiting the scope of the present application.

EXAMPLE 1

Preparation of Lactic Acid-producing Strain

In order to prepare a representative lactic-acid producing strain to be used in the present application, *Saccharomyces cerevisiae* CEN. PK2-1D, which is a representative yeast strain among the wild-type yeast strains obtained from Euroscarf, were subjected to a series of genetic manipulation.

Specifically, alcohol dehydrogenase 1 (ADH1) and pyruvate decarboxylase 1 (PDC1) were deleted for minimizing the fermentation of producing the alcohol, whereas for blocking the pathway of lactic acid decomposition, the strain with a deletion in D-lactate dehydrogenase 1 (DLD1) was used as the base strain of the present application.

DLD1 is not a factor that directly affects the improvement of growth but DLD1, being a dehydrogenase of D-type lactic acid, is known as a major enzyme that converts lactic acid into pyruvate using $NAD^+$. Accordingly, subsequent stains were prepared based on the strain with a deletion of the DLD1 gene, which is a lactic acid-consuming enzyme, and the lactic acid productivity was compared.

In the present application, the genetic manipulation was performed using a general molecular cloning method. First, the experiments on the deletion of ADH1 and PDC1 genes of the enzyme were performed using pWAL100 and pWBR100 plasmids based on the disclosure on the reference (Lee T H, et al., *J. Microbiol. Biotechnol.* (2006), 16 (6), 979-982). Each insert incorporated into each plasmid was prepared by polymerase chain reaction (PCR) using primers corresponding to each insert (SEQ ID NO: 1 to SEQ ID NO: 8).

PCR was performed while using the genomic DNA of wild-type yeast strains as a template. For the deletion of ADH1, PCR was performed using the primers of SEQ ID NO: 1 and SEQ ID NO: 2, and the resultant was cloned into pWAL100 using the restriction enzymes, BamHI and NcoI. Additional PCR was performed using the primers of SEQ ID NO: 3 and SEQ ID NO: 4 and the resultant was cloned into pWBR100 using the restriction enzymes, BamHI and NcoI. PCR was performed by denaturation at 95° C. for 5 min, annealing at 53° C. for 1 min, and polymerization at 72° C. for 1 min 30 sec.

For the deletion of PDC1, PCR was performed using the primers of SEQ ID NO: 5 and SEQ ID NO: 6, and the resultant was cloned into pWAL 100 using the restriction enzymes, BamHI and NcoI. Additional PCR was performed using the primers of SEQ ID NO: 7 and SEQ ID NO: 8 and the resultant was cloned into pWBR100 using the restriction enzymes, BamHI and NcoI. PCR was performed by denaturation at 95° C. for 5 min, annealing at 53° C. for 1 min, and polymerization at 72° C. for 1 min 30 sec.

Additionally, for the deletion of DLD1 gene, HIS3 marker gene was deleted by introduction via double crossover. The DNA fragments used therein were obtained by PCR performed using the genomic DNA of the wild-type yeast stain, along with primers of SEQ ID NO: 9 and SEQ ID NO: 10. PCR was performed by denaturation at 95° C. for 5 min, annealing at 53° C. for 1 min, and polymerization at 72° C. for 1 min 30 sec.

The primers used in the gene manipulation are summarized in Table 1 below.

Based on the strains having deletions of three genes (ADH1, PDC1, and DLD1), the D-lactate dehydrogenase (D-LDH) for lactic acid production was introduced. The 5' terminus and 3' terminus of ldhD gene derived from *Lb. plantarum* were respectively inserted to p413TEF1 vector so that the ldhD gene can be included between the TEF1 promoter and the CYC1 terminator derived from *S. cerevisiae*, in which the insert was prepared by a double digestion with SaxI/PvuII. The vector was made blunt-ended using Mungbean nuclease in the DNA fragments double-digested with BamHI/NotI of the p-δ-neo vector, and treated again with SacI, thereby generating the vector portion having a SacI sticky end and a BamHI blunt end.

The thus-obtained vector and the insert were ligated to complete the pTL573 vector and named as pTL573 vector. The pTL573 plasmid contains the ldhD gene derived from *Lb. plantarum* and was designed so that multiple copies can be randomly inserted into the δ-sequence, which is a part of the region of the retrotransposable element of *S. cerevisiae* CEN. PK2-1D pdc1 adh1 dld1 strain. For the multiple insertion of the corresponding gene, the pTL573 plasmid was digested with SacI to prepare a DNA fragment that can induce a single crossover in the δ-sequence. The resultant was introduced into a parent strain by transfection and numerous colonies were obtained in YPD (1% yeast extract, 2% bacto-peptone, and 2% glucose) medium in a maximum concentration of 5 mg/mL G418. It was confirmed that the thus-obtained strain was finally inserted with a multiple number of *Lb. plantarum*-derived D-LDH for providing D-type lactic acid productivity and the strain was named as CC02-0064.

TABLE 1

Primer sequences for preparation of base strains for lactic acid production

| Primer | Sequence (5'→3') |
| --- | --- |
| ADH1 upstream forward primer (SEQ ID NO: 1) | CGGGATCCACTGTAGCCCTAGACTTGATAGCC |
| ADH1 upstream reverse primer (SEQ ID NO: 2) | ATAAGAATGCGGCCGCTGTATATGAGATAGTTGATTGTATGCTT |
| ADH1 downstream forward primer (SEQ ID NO: 3) | GACTAGTGCGAATTTCTTATGATTTATGATTTTTATT |
| ADH1 downstream reverse primer (SEQ ID NO: 4) | ACATGCCATGgAAGCATGCACGTATACACTTGAGTAA |
| PDC1 upstream forward primer (SEQ ID NO: 5) | CGGGATCCATTATGTATGCTCTTCTGACTTTTCGT |
| PDC1 upstream reverse primer (SEQ ID NO: 6) | ATAAGAATGCGGCCGCTTTGATTGATTTGACTGTGTTATTTTGC |
| PDC1 downstream forward primer (SEQ ID NO: 7) | CGGGATCCGCGATTTAATCTCTAATTATTAGTTAAAG |
| PDC1 downstream reverse primer (SEQ ID NO: 8) | ATAAGAATGCGGCCGCTTTCAATCATTGGAGCAATCATTTTACA |
| DLD1-HIS3 upstream linking primer (SEQ ID NO: 9) | GCGTAGTTGGCCCCAACTGGTGCAGTAATACGTTTTAAGAGCTTGGTGAG |
| DLD1-HIS3 downstream linking primer (SEQ ID NO: 10) | CGTGAAGGGTGAAAAAGGAAAATCAGATACCTACATAAGAACACCTTTGG |

EXAMPLE 2

Preparation of Strains with Reduced Titer or Inactivated PDC

A strain with a reduced titer or inactivation of PDC was prepared by preparing a strain, which had a deletion of PDC5, i.e., a PDC isozyme, in the CC02-0064 strain, which is the base strain prepared in Example 1, and a strain which had deletions of both PDC5 and PDC6 in the CC02-0064 strain.

Specifically, for the deletion of the gene of a yeast, pWAL100 and pWBR100 plasmids (*J. Microbiol. Biotechnol.*, (2006) 16 (6), 979-982) were used.

For the deletion of PDC5, PCR was performed using the primers of SEQ ID NO: 11 and SEQ ID NO: 12 and the resultant was cloned into pWAL100 using the restriction enzymes, BamHI and NotI. Additional PCR was performed using the primers of SEQ ID NO: 13 and SEQ ID NO: 14 and the resultant was cloned into pWBR100 using the restriction enzymes, SpeI and NcoI. PCR was performed by denaturation at 95° C. for 5 min, annealing at 53° C. for 1 min, and polymerization at 72° C. for 1 min 30 sec.

For the deletion of PDC6, PCR was performed using the primers of SEQ ID NO: 15 and SEQ ID NO: 16 and the resultant was cloned into pWAL100 using the restriction enzymes, BamHI and NotI. Additional PCR was performed using the primers of SEQ ID NO: 17 and SEQ ID NO: 18 and the resultant was cloned into pWBR100 using the restriction enzymes, SpeI and NcoI. PCR was performed by denaturation at 95° C. for 5 min, annealing at 53° C. for 1 min, and polymerization at 72° C. for 1 min 30 sec.

TABLE 2

Primer sequences for deletion of PDC isozyme

| Primer | Sequence (5'→3') |
|---|---|
| F-ALPDC5-BamHI (SEQ ID NO: 11) | GAGCTCGGATCCAAGGAAATAAAGCAAATAACAATAACACC |
| R-ALPDC5-NotI (SEQ ID NO: 12) | ACCATGGCGGCCGCTTTGTTCTTCTTGTTATTGTATTGTGTTG |
| F-BRPDC5-SpeI (SEQ ID NO: 13) | GGATCCACTAGTGCTAATTAACATAAAACTCATGATTCAACG |
| R-BRPDC5-NcoI (SEQ ID NO: 14) | CAGCTGCCATGGTATTCTAAATAAGATGTAAGGCCTTGTAAT |
| F-ALPDC6-BamHI (SEQ ID NO: 15) | GAGCTCGGATCCATTAAAATCATGGAAATTATAGTATACAG |
| R-ALPDC6-NcoI (SEQ ID NO: 16) | CAGCTGCCATGGTTTGTTGGCAATATGTTTTTGCTATATTA |
| F-BRPDC6-BamHI (SEQ ID NO: 17) | GAGCTCGGATCCGCCATTAGTAGTGTACTCAAACGAATTA |
| R-BRPDC6-NcoI (SEQ ID NO: 18) | CAGCTGCCATGGACCTCAAAACATTCTTTTCAATCTTAACC |

The novel strains prepared above were named as CC02-0256 and CC02-0553, respectively, and the genetic traits of the novel strains are summarized in Table 3 below.

TABLE 3

Strains with reduced or inactivated PDC activities

| Strain | Genetic Traits |
|---|---|
| CC02-0256 | *Saccharomyces cerevisiae* δ:: ldhD adh1Δdld1Δ pdc1Δpdc5Δ |
| CC02-0553 | *Saccharomyces cerevisiae* δ:: ldhD adh1Δdld1Δ pdc1Δpdc5Δpdc6Δ |

EXAMPLE 3

Evaluation of Lactic Acid Productivity of Strains with Reduced or Inactivated PDC Activity The media used for the evaluation of strains were synthetic complex media (SC). For the preparation of the media, an amino acid dropout mix (Sigma) was mixed to the 0.67% yeast nitrogen base without amino acid, which was used as the base, according to the manufacturer's protocol, and the amino acids not included therein were added as necessary. Leucine was added to a concentration of 380 mg/L, and uracil, tryptophan, and histidine were added to a concentration of 76 mg/L, respectively, and glucose (8%) as a carbon source and 1% $CaCO_3$ as a neutralizing agent were added thereto. The thus-prepared media were used for the evaluation of lactic acid fermentation of yeast strains.

As the conditions for the evaluation of lactic acid fermentation ability of the strains, the media prepared for the evaluation of lactic acid fermentation were aliquoted in an amount of 25 mL per each flask and inoculated with each of the yeast strains, cultured at 30° C. aerobically for 48 hours, and the amount of lactic acid present in the fermentation liquid was analyzed by HPLC.

The results of the experiments are summarized in Table 4 below.

TABLE 4

Comparison of the results of fermentation of strains with reduced or inactivated PDC activities

| Strain | OD (600 nm) | Glucose Consumption (g/L) | Lactic Acid (g/L) | Yield (%) | Productivity (g/L/h) |
|---|---|---|---|---|---|
| CC02-0064 | 10.5 | 75.5 | 36.5 | 48.4 | 0.76 |
| CC02-0256 | 3.6 | 49.5 | 29.1 | 58.7 | 0.61 |
| CC02-0553 | 2.6 | 34.5 | 20.8 | 60.2 | 0.43 |

As a result, as can be confirmed from Table 4 above, the yield increased as the PDC activity reduced but the productivity was reduced.

EXAMPLE 4

Introduction of ATP-Citrate Lyase (ACL) Based on PDC-inactivated Strains and Preparation of Strains with Enhanced Activities of Phosphoenolpyruvate Carboxykinase 1 (PCK1) and Pyruvate Kinase 2 (PYK2)

(1) Preparation of a Vector for Introduction of a Foreign ACL into a Lactic-acid Producing Strain A recombinant vector for the introduction of a foreign ACL enzyme and the simultaneous overexpression of PCK1 and PYK2, one of the pathways of pyruvate biosynthesis, was prepared.

For the foreign ACL, a gene derived from *Mus musculus*, a mammal, was used and the corresponding gene was confirmed by NCBI (Accession no. NP_001186225).

Specifically, the gene was synthesized using the amino acid sequence of SEQ ID NO: 29 (or an amino acid sequence of SEQ ID NO: 30), the vector was prepared using the GPD promoter based on pRS415, a gene expression vector for yeasts, and the vector inserted with the gene was prepared and named as p415GPDpro-ACL.

(2) Preparation of a Vector with Enhanced PCK1 and PYK2 for Enhancement of Pyruvate Biosynthesis Pathway A recombinant vector for the simultaneous overexpression of PCK1 and PYK2 for the enhancement of pyruvate biosynthesis pathway was prepared.

PYK2 is a gene present in a yeast microorganism and may be represented by SEQ ID NO: 33. PCR was performed using the genomic DNA of *S. cerevisiae* as a template along with the primers of SEQ ID NOS: 19 and 20, and the fragments of PYK2 gene were obtained therefrom. PCR was performed by denaturation at 95° C. for 5 min, annealing at 53° C. for 1 min, and polymerization at 72° C. for 1 min 30 sec. The cloning was performed using the gene fragments and the restriction enzymes within the yeast expression vector derived from pRS416, i.e., SpeI, XhoI, and the overexpression was performed using the TEF1 promoter. The corresponding recombinant vector was named as pRS416-TEF1pro-PYK2.

PYK1 is also a gene present in a yeast microorganism and may be represented by SEQ ID NO: 31. PCR was performed using the genomic DNA of *S. cerevisiae* as a template along with the primers of SEQ ID NOS: 23 and 24, and the fragment of PYK1 gene were obtained therefrom. PCR was performed by denaturation at 95° C. for 5 min, annealing at 53° C. for 1 min, and polymerization at 72° C. for 1 min 30 sec. PCR was performed under the same conditions for obtaining the PCK1 fragment using the genomic DNA of *S. cerevisiae* as a template along with the primers of SEQ ID NOS: 21 and 22 so that PYK1 can be expressed using the TEF2 promoter, and the fragment of the TEF2 promoter were obtained. Then, for the simultaneous expression of PCK1 and PYK2 in a single recombinant vector, the pRS416-TEF1pro-PYK2 recombinant vector prepared above was digested with XhoI, and at the time, the fragment of the TEF2 promoter and the PCK1 fragment were cloned using the In-Fusion cloning kit (Clontech). Finally, a single recombinant vector which can overexpress PCK1 and PYK2 with the TEF2 promoter and the TEF1 promoter, respectively, and the vector was named as pRS416-TEF1pro-PYK2-TEF2pro-PCK1. The primers used in the preparation of the vector for the overexpression of PCK1 and PYK2 are summarized in Table 5 below.

TABLE 5

Primers used for the overexpression of PCK1 and PYK2

| Primer | Sequence (5'→3') |
| --- | --- |
| F-PYK2-SpeI (SEQ ID NO: 19) | AAAACTAGTATGCCAGAGTCCAGATTGCAGAGA |
| R-PYK2-XhoI (SEQ ID NO: 20) | AAAACTCGAGCTAGAATTCTTGACCAACAGTAGAAAT |
| F-PYK2-ADH1t-infusion (SEQ ID NO: 21) | TGTTGGTCAAGAATTCTAGGCGAATTTCTTATGATTTATGAT |
| R-TEF2p-PCK1-infusion (SEQ ID NO: 22) | TTCATTTTAGAAGGGGACATGTTTAGTTAATTATAGTTCGTTGAC |
| F-PCK1-TEF2-infusion (SEQ ID NO: 23) | AACGAACTATAATTAACTAAACATGTCCCCTTCTAAAATGAATGCT |
| R-PCK1-infusion (SEQ ID NO: 24) | ATAACTAATTACATGACTCGAGTTACTCGAATTGAGGACCAGCGGC |

(3) Introduction of a Foreign ACL into Lactic Acid-Producing Strains with Inactivated PDC, and Preparation of Strains with Enhanced Activities of PCK1 and PYK2

The foreign ACL prepared in Example 4-(1) based on the CC02-0553 strain prepared in Example 2 was introduced, and the vector for the simultaneous overexpression of PCK1/PYK2 prepared in Example 4-(2) was inserted by transfection.

The transfection was performed using a method, which includes treating the CC02-0553 strain cultured in YPD (1% yeast extract, 2% bacto-peptone, and 2% glucose) medium for 18 hours with a solution containing 0.1 M Lithum Acetate, 0.01 M Tris-HCl, and 0.001 M EDTA (hereinafter, LiAc/TE buffer), and heat-treated along with the LiAc/TE buffer containing 40% PEG at 42° C. for 15 minutes for the insertion of a recombinant vector. The thus-prepared strains were named as CC02-0652 and CC02-0765, respectively, and the genetic traits are summarized in Table 6 below.

TABLE 6

Introduction of ACL based on strains with inactivated PDC potency, and strains with enhanced activities of PCK1 and PYK2

| Strain | Genetic Traits |
| --- | --- |
| CC02-0652 | CC02-0553 pRS415-GPDpro-ACL |
| CC02-0765 | CC02-0553 pRS415-GPDpro-ACL, pRS416-TEF1p-PYK2-TEF2p-PCK1 |

EXAMPLE 5

Introduction of ACL Based on Inactivated PDC, and Evaluation on Fermentation in a Strain with Enhanced Activities of PCK1 and PYK2

For the evaluation of the ACL-PCK1-PYK2-enhanced strains, the lactic acid fermentation ability was evaluated in the strains with inactivated PDC potency prepared in Example 4-(3) in the same manner as in Example 3. The results are summarized in Table 7 below.

TABLE 7

Introduction of ACL based on strains with inactivated PDC titer and evaluation of strains with enhanced activities of PCK1 and PYK2

| Strain | OD (600 nm) | Glucose Consumption (g/L) | Lactic Acid (g/L) | Yield (%) | Productivity (g/L/h) |
|---|---|---|---|---|---|
| CC02-0553 | 2.6 | 34.5 | 20.8 | 60.2 | 0.43 |
| CC02-0652 | 5.0 | 56.0 | 31.6 | 62.5 | 0.66 |
| CC02-0765 | 6.1 | 69.1 | 45.6 | 66.0 | 0.95 |

As a result, as can be confirmed in Table 7 above, the strains, in which a foreign ACL was introduced and the activities of PCK1 and PYK2 were enhanced therein, showed an increase in $OD_{600}$ value, which represents the bacterial growth relative to the PDC-inactivated strain, by 130%; an increase in the amount of glucose consumption during the same period by 100%; and an improvement in the yield of lactic acid fermentation by 10%. Additionally, the strains finally showed an improvement of 120% in lactic acid productivity. Based on the fermentation result of the CC02-0652 strain, it was confirmed that the introduction of a foreign ACL could enhance the growth of yeast microorganisms due to acetyl-CoA production by a new production pathway. Additionally, it was confirmed that the introduction of a foreign ACL can not only enhance the growth but also increase the productivity.

Furthermore, by the result of the fermentation result of the CC02-0765 strain, it was confirmed that productivity of lactic acid fermentation can be further increased by the enhancement of pyruvate biosynthesis, and thus it was confirmed that the method for lactic acid production by the strategy of the present application employing acetyl-CoA production by a new pathway and enhancement of pyruvate biosynthesis is a method which can not only increase the lactic acid fermentation yield and enhance the growth of a given microorganism but also can increase the lactic acid fermentation productivity, unlike the existing technology.

Accordingly, the CC02-0765 strain was deposited in the Korean Culture Center of Microorganisms (KCCM) on Nov. 28, 2014, with the accession number KCCM11616P under the Budapest Treaty.

EXAMPLE 6

Introduction of ACL Based on PDC-inactivated Strains and Preparation of Strains with Enhanced Activities of Malate Dehydrogenase2 (MDH2) and Cytosolic Malic Enzyme 1 (MAE1)

Based on the result of Example 5, it was confirmed that the strategy of producing acetyl-CoA by a new pathway and enhancing pyruvate biosynthesis is an effective method for increasing the yield of lactic acid fermentation, enhancing the growth of a microorganism with productivity, and increasing the productivity of lactic acid fermentation, and as such, the present inventors have attempted to confirm whether the enhancement of pyruvate biosynthesis using other genes may have similar effects.

(1) Preparation of a Vector with Enhanced Activities of MDH2 and Cytosolic MAE1

Since the OAA produced by the introduction of a foreign ACL can be biosynthesized into pyruvate by a different pathway, the present inventors attempted to overexpress MDH2, which is originally located in the cytosol, and overexpress MAE1, which is an enzyme located in the mitochondria, by changing its location into the cytosol. To this end, a recombinant vector was prepared.

MDH2 is a gene present in yeast microorganisms and can be represented by an amino acid sequence of SEQ ID NO: 35. The fragment of the MDH2 gene was obtained by PCR which was performed using the genomic DNA of *S. cerevisiae* as a template along with the primers of SEQ ID NOS: 25 and 26. PCR was performed by denaturation at 95° C. for 5 min, annealing at 53° C. for 1 min, and polymerization at 72° C. for 1 min. The thus-obtained fragment of the MDH2 gene was cloned based on the pRS414 vector after digesting with restriction enzymes, SpeI and XhoI, in which the MDH2 gene was set up to be overexpressed using the TEF1 promoter. The thus-obtained recombinant vector was named as pRS414-TEF1pro-MDH2.

MAE1 is a gene originally present in the mitochondria of yeast microorganisms and can be represented by an amino acid sequence of SEQ ID NO: 37. For the expression of MAE1 gene in the cytosol, the MAE1 gene was cloned, excluding the mitochondrial target sequence (represented by the amino acid sequence of SEQ ID NO: 51), which consists of a sequence of 90 nucleotides from the start codon of the MAE1 gene. PCR was performed using the genomic DNA of *S. cerevisiae* as a template along with the primers of SEQ ID NOS: 27 and 28. PCR was performed by denaturation at 95° C. for 5 min, annealing at 53° C. for 1 min, and polymerization at 72° C. for 2 min. The thus-obtained PCR fragments were cloned based on the pRS416 vector after digesting with restriction enzymes, SpeI and XmaI. The primer of SEQ ID NO: 27 was prepared in such a manner to obtain the nucleotide sequences starting from the position 91, in order to remove the sequence of the 90 nucleotides starting from the MAE1 ORF start codon. Additionally, it was attempted to overexpress the cytosolic MAE1 using the TEF1 promoter. Additionally, the thus-prepared recombinant vector was named as pRS416-TEF1pro-cytosolic MAE1. The primers used for the preparation of the recombinant vectors, i.e., pRS414-TEF1pro-MDH2 and pRS416-TEF1pro-cytosolic MAE1, are summarized in Table 8 below.

TABLE 8

Primers for the overexpression of MDH2 and cytosolic MAE1

| Primer | Sequence (5'→3') |
|---|---|
| F-MDH2-SpeI (SEQ ID NO: 25) | CTAGAACTAGTATGCCTCACTCAGTTACACCATCCATA |
| R-MDH2-XhoI (SEQ ID NO: 26) | GGGGGCCCGGGTTAAGATGATGCAGATCTCGATGCAAC |
| F-cytMAE1-SpeI (SEQ ID NO: 27) | TTTCTAGAACTAGTATGTGGCCTATTCAGCAATCGCGTT |
| R-cytMAE1-XmaI (SEQ ID NO: 28) | AGAGACCCGGGCTACAATTGGTTGGTGTGCACCGAT |

(2) Preparation of Strains with Enhanced Activities of MDH2 and Cytosolic MAE1 in the Lactic Acid-producing Strain with Inactivated PDC The vector introduced with a foreign ACL prepared in Example 4-(1), and the MDH2 overexpression vector and the cytosolic MAE1 overexpression vector prepared in Example 6-(1) were cloned by transfection based on the CC02-0553 strain prepared in Example 2. The transfection was performed using the method explained in Example 4-(3). The thus-prepared strain was named as CC02-0821, and the genetic trait of the strain is summarized in Table 9 below.

TABLE 9

Introduction of ACL in a strain with inactivated PDC, and a strain with enhanced activity of MDH2 and cytosolic MAE1

| Strain | Genetic Traits |
|---|---|
| CC02-0821 | CC02-0553 pRS415-GPDpro-ACL, pRS414-TEF1pro-MDH2, pRS416-TEF1pro-cytosolic MAE1 |

EXAMPLE 7

Introduction of ACL Based on Strains with Inactivated PDC and Evaluation on Fermentation in Strains with Enhanced Activities of MDH2 and Cytosolic MAE1

For the evaluation on the ACL-MDH2-cytosolic MAE1-enhanced strains, the lactic acid fermentation ability was evaluated in the strains with inactivated PDC prepared in Example 6 in the same manner as in Example 2. The results are summarized in Table 10 below.

TABLE 10

Evaluation of fermentation ability of ACL-MDH2-cytosolic MAE1-enhanced strains based on strains with inactivated PDC

| Strain | OD (600 nm) | Glucose Consumption (g/L) | Lactic Acid (g/L) | Yield (%) | Productivity (g/L/h) |
|---|---|---|---|---|---|
| CC02-0553 | 2.6 | 34.5 | 20.8 | 60.2 | 0.43 |
| CC02-0652 | 5.0 | 56.0 | 31.6 | 62.5 | 0.66 |
| CC02-0821 | 5.4 | 62.1 | 39.7 | 64.0 | 0.82 |

As can be confirmed in Table 10 above, as a result of fermentation ability evaluation of the CC02-0821 strain, in which pyruvate biosynthesis was enhanced by overexpression of MDH2 and cytosolic MAE1, also showed an increase in $OD_{600}$ value, which represents the bacterial growth relative to the strain where the PDC activity was removed, by 110%; an increase in the amount of glucose consumption during the same period by 80%; and an improvement in the yield of lactic acid fermentation by 6%, as is the case with the CC02-0765 strain. Additionally, the strains finally showed an improvement of 90% in lactic acid productivity. Based on the results above, it was confirmed that not only the introduction of a foreign ACL for the improvement of lactic acid in a yeast microorganism but also the enhancement of pyruvate biosynthesis pathways via various routes is also effective for further improvement of lactic acid productivity.

EXAMPLE 8

Introduction of ACL in Strains with Reduced PDC Activity and Preparation of Strains with Enhanced Activities of PCK1 and PYK2, and Strains with Enhanced Activities of MDH2 and Cytosolic MAE1

Conclusively from the results in Examples, it was confirmed that the strains, in which PDC titer was removed, could increase the productivity of lactic acid fermentation by the introduction of a foreign ACL and the enhancement of pyruvate biosynthesis pathway. As such, the present inventors have attempted to confirm whether the same result could be obtained from the strains, in which the PDC titer was reduced, as well as in the strains, in which the PDC titer was removed.

The recombinant vectors, i.e., pRS415-GPDpro-ACL and pRS416-TEF1pro-PYK2-TEF2p-PCK1, prepared in Example 4 were inserted based on the CC02-0256 strain, which is a strain with reduced PDC activity prepared in Example 2, in the same manner as in Example 4-(3). The thus-prepared strains were named as CC02-0819 and CC02-0820, respectively. Furthermore, the recombinant vectors, i.e., pRS415-GPDpro-ACL prepared in Example 4 and pRS414-TEF1pro-MDH2 and pRS416-TEF1pro-cytosolic MAE1, prepared in Example 6-(1) were inserted based on the CC02-0256 strain, which is a strain with reduced PDC activity prepared in Example 2, in the same manner as in Example 4-(3). The thus-prepared strain was named as CC02-0831, and the genetic trait of the strain is summarized in Table 11 below.

TABLE 11

Introduction of ACL based on strains with reduced PDC activity and preparation of strains with enhanced pyruvate biosynthesis pathway

| Strain | Genetic Traits |
|---|---|
| CC02-0819 | CC02-0256 pRS415-GPDpro-ACL |
| CC02-0820 | CC02-0256 pRS415-GPDpro-ACL, pRS416-TEF1p-PYK2-TEF2p-PCK1 |
| CC02-0831 | CC02-0256 pRS415-GPDpro-ACL, pRS414-TEF1pro-MDH2, pRS416-TEF1pro-cytosolic MAE1 |

EXAMPLE 9

Introduction of ACL in Strains with Reduced PDC Activity and Evaluation on Fermentation in Strains with Enhanced Activities of PCK1 and PYK2

The lactic acid fermentation ability of CC02-0819 and CC02-0820 strains prepared in Example 8 was evaluated along with the CC02-0256 strain, which is a control group, in the same manner as in Example 3. The results of the experiments are summarized in Table 12 below.

TABLE 12

Introduction of ACL based on strains with reduced PDC activity and evaluation of the fermentation of strains with enhanced activities of PCK1 and PYK2

| Strain | OD (600 nm) | Glucose Consumption (g/L) | Lactic Acid (g/L) | Yield (%) | Productivity (g/L/h) |
|---|---|---|---|---|---|
| CC02-0256 | 3.6 | 49.5 | 29.1 | 58.7 | 0.61 |
| CC02-0819 | 5.9 | 60.1 | 35.7 | 59.4 | 0.74 |
| CC02-0820 | 6.6 | 69.8 | 41.9 | 60.1 | 0.87 |

As a result, as can be confirmed in Table 12 above, the CC02-0256 strain did not show a significant increase in effects by increasing the introduction of a foreign ACL and enhancing the pyruvate biosynthesis pathway, unlike in the CC02-0553 strain, but there were an improvement in lactic acid fermentation yield, an increase in bacterial growth of microorganisms with productivity, and an increase in productivity of lactic acid fermentation as well.

The CC02-0820 strain, in which a foreign ACL was introduced and PCK1 and PYK2 activities were enhanced, showed an increase in $OD_{600}$ value, which represents the bacterial growth relative to the strain with reduced PDC titer, by 80%; an increase in the amount of glucose consumption during the same period by 40%; and an improvement in the yield of lactic acid fermentation by 2%. Additionally, the lactic acid productivity was finally improved by 40%. The CC02-0820 strain showed increases in all of the OD value, the amount of glucose consumption during the same period, and the yield of lactic acid fermentation, compared to the CC02-0819 strain, which was introduced with a foreign ACL only, and showed a 20% increase in productivity.

EXAMPLE 10

Introduction of ACL in Strains with Reduced PDC Activity and Comparative Evaluation on Fermentation in Strains with Enhanced Activities of MDH2 and Cytosolic MAE1

The CC02-0831 strain prepared in Example 8 was evaluated along with the CC02-0256 and CC02-0819 strains, which are control groups, in the same manner as in Example 3. The results of the experiments are summarized in Table 13 below.

TABLE 13

Introduction of ACL based on strains with reduced PDC titer and evaluation of the fermentation of strains with enhanced activities of MDH2 and cytosolic MAE1

| Strain | OD (600 nm) | Glucose Consumption (g/L) | Lactic Acid (g/L) | Yield (%) | Productivity (g/L/h) |
|---|---|---|---|---|---|
| CC02-0256 | 3.6 | 49.5 | 29.1 | 58.7 | 0.61 |
| CC02-0819 | 5.9 | 60.1 | 35.7 | 59.4 | 0.74 |
| CC02-0831 | 6.3 | 66.2 | 39.8 | 60.1 | 0.82 |

As a result, as can be confirmed in Table 13 above, the CC02-0831 strain, in which a foreign ACL was introduced and MDH2 and cytosolic MAE1 activities were enhanced, showed an increase in the $OD_{600}$ value relative to that of the parent strain, CC02-0256, by 80%, an increase in the amount of glucose consumption during the same period by 30%; and an improvement in the yield of lactic acid fermentation by 2%. Additionally, the lactic acid productivity was finally improved by 30%. The CC02-0831 strain showed increases in all of the OD value, the amount of glucose consumption during the same period, and the yield of lactic acid fermentation, compared to the CC02-0819 strain, which was introduced with a foreign ACL only, and showed a 20% increase in productivity.

The above results support that the method for lactic acid production by the strategy employing the acetyl-CoA production by a new pathway and enhanced pyruvate biosynthesis is a method, which can not only increase the yield of lactic acid fermentation and the enhancement of the growth of the microorganism with productivity, but also can increase the productivity of lactic acid fermentation, unlike the existing technology. In particular, the results suggest that the microorganism, which was prepared by the strategy of employing the acetyl-CoA production by a new pathway due to the introduction of a foreign ACL and enhanced pyruvate biosynthesis, can not only increase the yield of lactic acid fermentation and the enhancement of the growth of the microorganism with productivity, but also can increase the productivity of lactic acid fermentation, and thus can be provided as an excellent lactic acid-producing microorganism.

From the foregoing, a skilled person in the art to which the present application pertains will be able to understand that the present application may be embodied in other specific forms without modifying the technical concepts or essential characteristics of the present application. In this regard, the exemplary embodiments disclosed herein are only for illustrative purposes and should not be construed as limiting the scope of the present application. On the contrary, the present application is intended to cover not only the exemplary embodiments but also various alternatives, modifications, equivalents and other embodiments that may be included within the spirit and scope of the present application as defined by the appended claims.

The invention claimed is:

1. A microorganism of the genus *Saccharomyces* producing lactic acid, wherein the microorganism is modified to have inactivated activity of pyruvate decarboxylase (PDC) compared to its endogenous activity, to introduce the activity of ATP-citrate lyase (ACL), and to enhance pyruvate biosynthetic pathway compared to its endogenous biosynthetic pathway.

2. The microorganism according to the claim 1, wherein the enhancement of pyruvate biosynthetic pathway is achieved by enhancing the activity of phosphoenolpyruvate carboxykinase 1 (PCK1), pyruvate kinase 2 (PYK2) or the activities of both, compared to their endogenous activities.

3. The microorganism according to the claim 1, wherein the enhancement of pyruvate biosynthetic pathway is achieved by enhancing the activity of malate dehydrogenase 2 (MDH2), cytosolic malic enzyme 1 (cytosolic MAE1) or the activities of both, compared to their endogenous activities.

4. The microorganism according to the claim 1, wherein pyruvate decarboxylase is an enzyme represented by at least one amino acid sequence selected from the group consisting of amino acid sequences of SEQ ID NOS: 39, 41, and 43.

5. The microorganism according to the claim 1, wherein ATP-citrate lyase is an enzyme represented by an amino acid sequence of SEQ ID NO. 29.

6. The microorganism according to the claim 2, wherein phosphoenolpyruvate carboxykinase 1 is an enzyme represented by an amino acid sequence of SEQ ID NO: 31 and pyruvate kinase 2 is an enzyme represented by an amino acid sequence of SEQ ID NO: 33.

7. The microorganism according to the claim 3, wherein malate dehydrogenase 2 is an enzyme represented by an amino acid sequence of SEQ ID NO: 35 and cytosolic malic enzyme 1 is an enzyme represented by an amino acid sequence of SEQ ID NO: 37 or SEQ ID NO: 52.

8. The microorganism according to the claim 1, wherein the microorganism is further modified to introduce the activity of lactate dehydrogenase (LDH).

9. The microorganism according to the claim 8, wherein the lactate dehydrogenase is an enzyme represented by an amino acid sequence of SEQ ID NO: 49.

10. The microorganism according to the claim 1, wherein the microorganism is further modified:
    (i) to inactivate the activity of alcohol dehydrogenase 1 (ADH1) compared to its endogenous activity;
    (ii) to inactivate the activity of pyruvate decarboxylase 1 (PDC1) compared to its endogenous activity; and
    (iii) to inactivate the activity of D-lactate dehydrogenase 1 (DLD1) compared to its endogenous activity.

11. The microorganism according to the claim 1, wherein the microorganism of the genus *Saccharomyces* is *Saccharomyces cerevisiae*.

12. A method for producing lactic acid comprising:
    a) culturing the microorganism of the genus *Saccharomyces* of claim 1 in a medium; and
    b) recovering lactic acid from the cultured microorganism or the medium.

* * * * *

SEQUENCE LISTING

```
<160> NUMBER OF SEQ ID NOS: 52

<210> SEQ ID NO 1
<211> LENGTH: 32
<212> TYPE: DNA
<213> ORGANISM: Artificial Sequence
<220> FEATURE:
<223> OTHER INFORMATION: ADH1 upstream forward primer

<400> SEQUENCE: 1
cgggatccac tgtagcccta gacttgatag cc                                  32

<210> SEQ ID NO 2
<211> LENGTH: 44
<212> TYPE: DNA
<213> ORGANISM: Artificial Sequence
<220> FEATURE:
<223> OTHER INFORMATION: ADH1 upstream reverse primer

<400> SEQUENCE: 2
```
ataagaatgc ggccgctgta tatgagatag ttgattgtat gctt                    44

<210> SEQ ID NO 3
<211> LENGTH: 37
<212> TYPE: DNA
<213> ORGANISM: Artificial Sequence
<220> FEATURE:
<223> OTHER INFORMATION: ADH1 downstream forward primer

<400> SEQUENCE: 3
gactagtgcg aatttcttat gatttatgat ttttatt                            37

<210> SEQ ID NO 4
<211> LENGTH: 37
<212> TYPE: DNA
<213> ORGANISM: Artificial Sequence
<220> FEATURE:
<223> OTHER INFORMATION: ADH1 downstream reverse primer

<400> SEQUENCE: 4
acatgccatg gaagcatgca cgtatacact tgagtaa                            37

<210> SEQ ID NO 5
<211> LENGTH: 35
<212> TYPE: DNA
<213> ORGANISM: Artificial Sequence
<220> FEATURE:
<223> OTHER INFORMATION: PDC1 upstream forward primer

<400> SEQUENCE: 5
cgggatccat tatgtatgct cttctgactt ttcgt                              35

<210> SEQ ID NO 6
<211> LENGTH: 44
<212> TYPE: DNA
<213> ORGANISM: Artificial Sequence
<220> FEATURE:
<223> OTHER INFORMATION: PDC1 upstream reverse primer

<400> SEQUENCE: 6
ataagaatgc ggccgctttg attgatttga ctgtgttatt ttgc                    44

<210> SEQ ID NO 7
<211> LENGTH: 37
<212> TYPE: DNA
<213> ORGANISM: Artificial Sequence
<220> FEATURE:
<223> OTHER INFORMATION: PDC1 downstream forward primer

<400> SEQUENCE: 7
cgggatccgc gatttaatct ctaattatta gttaaag                            37

<210> SEQ ID NO 8
<211> LENGTH: 44
<212> TYPE: DNA
<213> ORGANISM: Artificial Sequence
<220> FEATURE:
<223> OTHER INFORMATION: PDC1 downstream reverse primer

<400> SEQUENCE: 8
ataagaatgc ggccgctttc aatcattgga gcaatcattt taca                    44

<210> SEQ ID NO 9
<211> LENGTH: 50
<212> TYPE: DNA
<213> ORGANISM: Artificial Sequence

```
<220> FEATURE:
<223> OTHER INFORMATION: DLD1-HIS3 upstream linking primer

<400> SEQUENCE: 9
gcgtagttgg ccccaactgg tgcagtaata cgttttaaga gcttggtgag          50

<210> SEQ ID NO 10
<211> LENGTH: 50
<212> TYPE: DNA
<213> ORGANISM: Artificial Sequence
<220> FEATURE:
<223> OTHER INFORMATION: DLD1-HIS3 downstream linking primer

<400> SEQUENCE: 10
cgtgaagggt gaaaaaggaa aatcagatac ctacataaga acacctttgg          50

<210> SEQ ID NO 11
<211> LENGTH: 41
<212> TYPE: DNA
<213> ORGANISM: Artificial Sequence
<220> FEATURE:
<223> OTHER INFORMATION: F-ALPDC5-BamHI primer

<400> SEQUENCE: 11
gagctcggat ccaaggaaat aaagcaaata acaataacac c                   41

<210> SEQ ID NO 12
<211> LENGTH: 43
<212> TYPE: DNA
<213> ORGANISM: Artificial Sequence
<220> FEATURE:
<223> OTHER INFORMATION: R-ALPDC5-NotI primer

<400> SEQUENCE: 12
accatggcgg ccgctttgtt cttcttgtta ttgtattgtg ttg                 43

<210> SEQ ID NO 13
<211> LENGTH: 42
<212> TYPE: DNA
<213> ORGANISM: Artificial Sequence
<220> FEATURE:
<223> OTHER INFORMATION: F-BRPDC5-SpeI primer

<400> SEQUENCE: 13
ggatccacta gtgctaatta acataaaact catgattcaa cg                  42

<210> SEQ ID NO 14
<211> LENGTH: 42
<212> TYPE: DNA
<213> ORGANISM: Artificial Sequence
<220> FEATURE:
<223> OTHER INFORMATION: R-BRPDC5-NcoI primer

<400> SEQUENCE: 14
cagctgccat ggtattctaa ataagatgta aggccttgta at                  42

<210> SEQ ID NO 15
<211> LENGTH: 41
<212> TYPE: DNA
<213> ORGANISM: Artificial Sequence
<220> FEATURE:
<223> OTHER INFORMATION: F-ALPDC6-BamHI primer

<400> SEQUENCE: 15
gagctcggat ccattaaaat catggaaatt aagtattaca g                   41
```

<210> SEQ ID NO 16
<211> LENGTH: 41
<212> TYPE: DNA
<213> ORGANISM: Artificial Sequence
<220> FEATURE:
<223> OTHER INFORMATION: R-ALPDC6-NcoI primer

<400> SEQUENCE: 16
cagctgccat ggtttgttgg caatatgttt ttgctatatt a                41

<210> SEQ ID NO 17
<211> LENGTH: 40
<212> TYPE: DNA
<213> ORGANISM: Artificial Sequence
<220> FEATURE:
<223> OTHER INFORMATION: F-BRPDC6-BamHI primer

<400> SEQUENCE: 17
gagctcggat ccgccattag tagtgtactc aaacgaatta                 40

<210> SEQ ID NO 18
<211> LENGTH: 41
<212> TYPE: DNA
<213> ORGANISM: Artificial Sequence
<220> FEATURE:
<223> OTHER INFORMATION: R-BRPDC6-NcoI primer

<400> SEQUENCE: 18
cagctgccat ggacctcaaa acattctttt caatcttaac c                41

<210> SEQ ID NO 19
<211> LENGTH: 33
<212> TYPE: DNA
<213> ORGANISM: Artificial Sequence
<220> FEATURE:
<223> OTHER INFORMATION: F-PYK2-SpeI primer

<400> SEQUENCE: 19
aaaactagta tgccagagtc cagattgcag aga                        33

<210> SEQ ID NO 20
<211> LENGTH: 37
<212> TYPE: DNA
<213> ORGANISM: Artificial Sequence
<220> FEATURE:
<223> OTHER INFORMATION: R-PYK2-XhoI primer

<400> SEQUENCE: 20
aaaactcgag ctagaattct tgaccaacag tagaaat                    37

<210> SEQ ID NO 21
<211> LENGTH: 42
<212> TYPE: DNA
<213> ORGANISM: Artificial Sequence
<220> FEATURE:
<223> OTHER INFORMATION: F-PYK2-ADH1t-infusion primer

<400> SEQUENCE: 21
tgttggtcaa gaattctagg cgaatttctt atgatttatg at              42

<210> SEQ ID NO 22
<211> LENGTH: 45
<212> TYPE: DNA
<213> ORGANISM: Artificial Sequence
<220> FEATURE:
<223> OTHER INFORMATION: R-TEF2p-PCK1-infusion primer

<400> SEQUENCE: 22
ttcattttag aaggggacat gtttagttaa ttatagttcg ttgac　　　　　　　　　　　45

<210> SEQ ID NO 23
<211> LENGTH: 46
<212> TYPE: DNA
<213> ORGANISM: Artificial Sequence
<220> FEATURE:
<223> OTHER INFORMATION: F-PCK1-TEF2-infusion primer

<400> SEQUENCE: 23
aacgaactat aattaactaa acatgtcccc ttctaaaatg aatgct　　　　　　　　　46

<210> SEQ ID NO 24
<211> LENGTH: 46
<212> TYPE: DNA
<213> ORGANISM: Artificial Sequence
<220> FEATURE:
<223> OTHER INFORMATION: R-PCK1-infusion primer

<400> SEQUENCE: 24
ataactaatt acatgactcg agttactcga attgaggacc agcggc　　　　　　　　　46

<210> SEQ ID NO 25
<211> LENGTH: 38
<212> TYPE: DNA
<213> ORGANISM: Artificial Sequence
<220> FEATURE:
<223> OTHER INFORMATION: F-MDH2-SpeI primer

<400> SEQUENCE: 25
ctagaactag tatgcctcac tcagttacac catccata　　　　　　　　　　　　　38

<210> SEQ ID NO 26
<211> LENGTH: 38
<212> TYPE: DNA
<213> ORGANISM: Artificial Sequence
<220> FEATURE:
<223> OTHER INFORMATION: R-MDH2-XhoI primer

<400> SEQUENCE: 26
gggggcccgg gttaagatga tgcagatctc gatgcaac　　　　　　　　　　　　　38

<210> SEQ ID NO 27
<211> LENGTH: 39
<212> TYPE: DNA
<213> ORGANISM: Artificial Sequence
<220> FEATURE:
<223> OTHER INFORMATION: F-cytMAE1-SpeI primer

<400> SEQUENCE: 27
tttctagaac tagtatgtgg cctattcagc aatcgcgtt　　　　　　　　　　　　39

<210> SEQ ID NO 28
<211> LENGTH: 36
<212> TYPE: DNA
<213> ORGANISM: Artificial Sequence
<220> FEATURE:
<223> OTHER INFORMATION: R-cytMAE1-XmaI primer

<400> SEQUENCE: 28
agagacccgg gctacaattg gttggtgtgc accgat　　　　　　　　　　　　　　36

<210> SEQ ID NO 29

<211> LENGTH: 1091
<212> TYPE: PRT
<213> ORGANISM: Mus musculus

<400> SEQUENCE: 29

Met Ser Ala Lys Ala Ile Ser Glu Gln Thr Gly Lys Glu Leu Leu Tyr
1               5                   10                  15

Lys Tyr Ile Cys Thr Thr Ser Ala Ile Gln Asn Arg Phe Lys Tyr Ala
            20                  25                  30

Arg Val Thr Pro Asp Thr Asp Trp Ala His Leu Leu Gln Asp His Pro
        35                  40                  45

Trp Leu Leu Ser Gln Ser Leu Val Val Lys Pro Asp Gln Leu Ile Lys
    50                  55                  60

Arg Arg Gly Lys Leu Gly Leu Val Gly Val Asn Leu Ser Leu Asp Gly
65                  70                  75                  80

Val Lys Ser Trp Leu Lys Pro Arg Leu Gly His Glu Ala Thr Val Gly
                85                  90                  95

Lys Ala Lys Gly Phe Leu Lys Asn Phe Leu Ile Glu Pro Phe Val Pro
            100                 105                 110

His Ser Gln Ala Glu Glu Phe Tyr Val Cys Ile Tyr Ala Thr Arg Glu
        115                 120                 125

Gly Asp Tyr Val Leu Phe His His Glu Gly Gly Val Asp Val Gly Asp
    130                 135                 140

Val Asp Ala Lys Ala Gln Lys Leu Leu Val Gly Val Asp Glu Lys Leu
145                 150                 155                 160

Asn Thr Glu Asp Ile Lys Arg His Leu Leu Val His Ala Pro Glu Asp
                165                 170                 175

Lys Lys Glu Val Leu Ala Ser Phe Ile Ser Gly Leu Phe Asn Phe Tyr
            180                 185                 190

Glu Asp Leu Tyr Phe Thr Tyr Leu Glu Ile Asn Pro Leu Val Val Thr
        195                 200                 205

Lys Asp Gly Val Tyr Ile Leu Asp Leu Ala Ala Lys Val Asp Ala Thr
    210                 215                 220

Ala Asp Tyr Ile Cys Lys Val Lys Trp Gly Asp Ile Glu Phe Pro Pro
225                 230                 235                 240

Pro Phe Gly Arg Glu Ala Tyr Pro Glu Glu Ala Tyr Ile Ala Asp Leu
                245                 250                 255

Asp Ala Lys Ser Gly Ala Ser Leu Lys Leu Thr Leu Leu Asn Pro Lys
            260                 265                 270

Gly Arg Ile Trp Thr Met Val Ala Gly Gly Ala Ser Val Val Tyr
    275                 280                 285

Ser Asp Thr Ile Cys Asp Leu Gly Gly Val Asn Glu Leu Ala Asn Tyr
290                 295                 300

Gly Glu Tyr Ser Gly Ala Pro Ser Glu Gln Gln Thr Tyr Asp Tyr Ala
305                 310                 315                 320

Lys Thr Ile Leu Ser Leu Met Thr Arg Glu Lys His Pro Glu Gly Lys
            325                 330                 335

Ile Leu Ile Ile Gly Gly Ser Ile Ala Asn Phe Thr Asn Val Ala Ala
        340                 345                 350

Thr Phe Lys Gly Ile Val Arg Ala Ile Arg Asp Tyr Gln Gly Pro Leu
    355                 360                 365

Lys Glu His Glu Val Thr Ile Phe Val Arg Arg Gly Gly Pro Asn Tyr
370                 375                 380

Gln Glu Gly Leu Arg Val Met Gly Glu Val Gly Lys Thr Thr Gly Ile

-continued

```
            385                 390                 395                 400
        Pro Ile His Val Phe Gly Thr Glu Thr His Met Thr Ala Ile Val Gly
                            405                 410                 415
        Met Ala Leu Gly His Arg Pro Ile Pro Asn Gln Pro Pro Thr Ala Ala
                            420                 425                 430
        His Thr Ala Asn Phe Leu Leu Asn Ala Ser Gly Ser Thr Ser Thr Pro
                            435                 440                 445
        Ala Pro Ser Arg Thr Ala Ser Phe Ser Glu Ser Arg Ala Asp Glu Val
        450                 455                 460
        Ala Pro Ala Lys Lys Ala Lys Pro Ala Met Pro Gln Gly Lys Ser Ala
        465                 470                 475                 480
        Thr Leu Phe Ser Arg His Thr Lys Ala Ile Val Trp Gly Met Gln Thr
                            485                 490                 495
        Arg Ala Val Gln Gly Met Leu Asp Phe Asp Tyr Val Cys Ser Arg Asp
                            500                 505                 510
        Glu Pro Ser Val Ala Ala Met Val Tyr Pro Phe Thr Gly Asp His Lys
                            515                 520                 525
        Gln Lys Phe Tyr Trp Gly His Lys Glu Ile Leu Ile Pro Val Phe Lys
                            530                 535                 540
        Asn Met Ala Asp Ala Met Lys Lys His Pro Glu Val Asp Val Leu Ile
        545                 550                 555                 560
        Asn Phe Ala Ser Leu Arg Ser Ala Tyr Asp Ser Thr Met Glu Thr Met
                            565                 570                 575
        Asn Tyr Ala Gln Ile Arg Thr Ile Ala Ile Ala Glu Gly Ile Pro
                            580                 585                 590
        Glu Ala Leu Thr Arg Lys Leu Ile Lys Lys Ala Asp Gln Lys Gly Val
                            595                 600                 605
        Thr Ile Ile Gly Pro Ala Thr Val Gly Gly Ile Lys Pro Gly Cys Phe
                            610                 615                 620
        Lys Ile Gly Asn Thr Gly Gly Met Leu Asp Asn Ile Leu Ala Ser Lys
        625                 630                 635                 640
        Leu Tyr Arg Pro Gly Ser Val Ala Tyr Val Ser Arg Ser Gly Gly Met
                            645                 650                 655
        Ser Asn Glu Leu Asn Asn Ile Ile Ser Arg Thr Thr Asp Gly Val Tyr
                            660                 665                 670
        Glu Gly Val Ala Ile Gly Gly Asp Arg Tyr Pro Gly Ser Thr Phe Met
                            675                 680                 685
        Asp His Val Leu Arg Tyr Gln Asp Thr Pro Gly Val Lys Met Ile Val
                            690                 695                 700
        Val Leu Gly Glu Ile Gly Gly Thr Glu Glu Tyr Lys Ile Cys Arg Gly
        705                 710                 715                 720
        Ile Lys Glu Gly Arg Leu Thr Lys Pro Val Val Cys Trp Cys Ile Gly
                            725                 730                 735
        Thr Cys Ala Thr Met Phe Ser Ser Glu Val Gln Phe Gly His Ala Gly
                            740                 745                 750
        Ala Cys Ala Asn Gln Ala Ser Glu Thr Ala Val Ala Lys Asn Gln Ala
                            755                 760                 765
        Leu Lys Glu Ala Gly Val Phe Val Pro Arg Ser Phe Asp Glu Leu Gly
                            770                 775                 780
        Glu Ile Ile Gln Ser Val Tyr Glu Asp Leu Val Ala Lys Gly Ala Ile
        785                 790                 795                 800
        Val Pro Ala Gln Glu Val Pro Pro Pro Thr Val Pro Met Asp Tyr Ser
                            805                 810                 815
```

-continued

Trp Ala Arg Glu Leu Gly Leu Ile Arg Lys Pro Ala Ser Phe Met Thr
            820                 825                 830

Ser Ile Cys Asp Glu Arg Gly Gln Glu Leu Ile Tyr Ala Gly Met Pro
        835                 840                 845

Ile Thr Glu Val Phe Lys Glu Glu Met Gly Ile Gly Gly Val Leu Gly
    850                 855                 860

Leu Leu Trp Phe Gln Arg Arg Leu Pro Lys Tyr Ser Cys Gln Phe Ile
865                 870                 875                 880

Glu Met Cys Leu Met Val Thr Ala Asp His Gly Pro Ala Val Ser Gly
                885                 890                 895

Ala His Asn Thr Ile Ile Cys Ala Arg Ala Gly Lys Asp Leu Val Ser
                900                 905                 910

Ser Leu Thr Ser Gly Leu Leu Thr Ile Gly Asp Arg Phe Gly Gly Ala
            915                 920                 925

Leu Asp Ala Ala Ala Lys Met Phe Ser Lys Ala Phe Asp Ser Gly Ile
        930                 935                 940

Ile Pro Met Glu Phe Val Asn Lys Met Lys Lys Glu Gly Lys Leu Ile
945                 950                 955                 960

Met Gly Ile Gly His Arg Val Lys Ser Ile Asn Asn Pro Asp Met Arg
                965                 970                 975

Val Gln Ile Leu Lys Asp Phe Val Lys Gln His Phe Pro Ala Thr Pro
            980                 985                 990

Leu Leu Asp Tyr Ala Leu Glu Val Glu Lys Ile Thr Thr Ser Lys Lys
        995                 1000                1005

Pro Asn Leu Ile Leu Asn Val Asp Gly Phe Ile Gly Val Ala Phe Val
    1010                1015                1020

Asp Met Leu Arg Asn Cys Gly Ser Phe Thr Arg Glu Glu Ala Asp Glu
1025                1030                1035                1040

Tyr Val Asp Ile Gly Ala Leu Asn Gly Ile Phe Val Leu Gly Arg Ser
                1045                1050                1055

Met Gly Phe Ile Gly His Tyr Leu Asp Gln Lys Arg Leu Lys Gln Gly
                1060                1065                1070

Leu Tyr Arg His Pro Trp Asp Asp Ile Ser Tyr Val Leu Pro Glu His
        1075                1080                1085

Met Ser Met
    1090

<210> SEQ ID NO 30
<211> LENGTH: 3276
<212> TYPE: DNA
<213> ORGANISM: Mus musculus
<220> FEATURE:
<221> NAME/KEY: gene
<222> LOCATION: (1)..(1091)
<223> OTHER INFORMATION: ACL

<400> SEQUENCE: 30
atgtcagcca aggcaatttc agagcagacc ggcaaagaac tcctgtacaa gtacatctgc      60
accacctcgg ccatccagaa ccggttcaag tacgcccggg tgactcccga cacagactgg     120
gcccatctgc tgcaggacca cccgtggctg ctcagccaga gcttggttgt caagccagac     180
cagttaatca aacgtcgagg aaagcttggc ctcgtcgggg tcaatctctc tctggatgga     240
gtcaaatcct ggctaaaacc tcgcctggga catgaagcca ctgtcggcaa ggccaaaggc     300
ttcctcaaga actttctcat tgaacccttc gtccccaca gtcaggcgga ggagttctac     360

```
gtgtgcatct atgctacccg ggaaggagac tacgtcctgt tccaccatga agggggtgtg    420
gatgtgggcg atgtggatgc caaagcccag aagctgcttg tgggtgtgga cgaaaagctg    480
aataccgagg acattaagag acacctgttg gtccatgcac ctgaggacaa gaaagaagtc    540
ctggccagct tcatctctgg tctattcaat ttctacgagg atctgtactt cacctacctt    600
gagatcaacc cccttgtggt gaccaaagat ggtgtctaca tccttgactt ggcggccaag    660
gtggatgcca cagctgacta catctgtaaa gtcaagtggg gtgatataga gttccctccc    720 cccttgggc gtgaggcgta ccccgaggaa gcctacattg cagacctgga tgccaaaagt     780
ggagcaagct tgaagctgac cttgctgaac cccaaggggc ggatctggac catggttgct    840
gggggtggcg cctccgtcgt gtacagtgac accatctgtg atcttggagg tgtcaatgaa    900
ctggcgaatt acgggaata ctcgggtgcc cccagtgaac aacagaccta tgactatgcc     960
aagaccatcc tctcacttat gactcgagag aagcacccag aaggcaagat cctcatcatt   1020
ggaggcagca ttgcaaactt caccaatgtg ccgccacct tcaagggcat tgtgagagcg    1080
attcgagatt accagggtcc cctgaaggag catgaggtca ccatctttgt ccgaagaggt   1140
ggccccaact atcaagaggg attacgagtg atgggagaag ttgggaagac cactgggatc   1200
cccatccatg tctttggcac agaaactcac atgacggcca ttgtgggcat ggccctgggc   1260
caccggccca ttcccaacca gccacccaca gcagctcaca ctgccaactt cctccttaat   1320
gccagcggga gcacatcgac tccagcaccc agtaggacag catctttttc tgagtcccga   1380
gctgatgaag tggcacctgc aaagaaagcc aagccagcta tgccccaagg aaagagtgcc   1440
accctcttca gccgacatac caaggccatc gtgtggggca tgcagacccg ggctgtgcag   1500
ggcatgctgg actttgacta cgtgtgttcc cgagacgagc cctcagtggc tgccatggtc   1560 tacccttca ctggggatca caagcagaag ttttactggg gacacaagga aatcctgatc    1620
cctgtcttca agaacatggc tgacgccatg aagaagcacc cggaggtaga cgtgctgatc   1680
aactttgcgt ctctgcggtc cgcttacgac agcaccatgg agaccatgaa ctatgcccag   1740
atccgcacca tagccatcat agcagaaggt atccctgagg ccctcacacg gaagctcatc   1800
aagaaggccg accagaaggg agtgaccatc attgggccag ctacggttgg gggcattaag   1860
cctggatgct ttaagatcgg gaatactggt ggaatgctgg acaacatcct ggcctccaaa   1920
ctgtaccgcc caggcagcgt ggcctacgtc tcacgttcag gaggcatgtc taatgaactc   1980
aataacatca tctctcggac cacagatggt gtctatgagg gcgtggccat cggcggggac   2040
aggtaccctg gtccacatt catggatcac gtgctgcgct accaggacac tccaggagtc    2100
aagatgatcg tagttcttgg ggagatagg ggcacagagg aatataagat ctgccggggc    2160
atcaaggagg gccgcctcac caagccagtg gtctgctggt gtatcgggac ctgtgccacc   2220
atgttctcct ccgaggtcca gtttggccat gctggagctt gtgccaacca ggcttctgaa   2280
actgcagtag ccaagaacca ggccttgaag gaagcaggag tgtttgtgcc ccgaagcttc   2340
gatgagcttg agaaatcat tcagtctgtg tatgaagatc tggtggccaa aggagccatt    2400
gtacctgccc aggaagtgcc acctccaaca gtgcccatgg actactcttg ggccagagag   2460
ctgggtttga tccgaaaacc tgcctcattc atgaccagca tctgtgatga gcgagggcag   2520
gagctcattt atgcgggcat gcccatcacc gaggtcttca aggaggagat gggcatcggt   2580
ggtgtcctcg gcctcctctg gttccagaga aggttgccca gtattcctg ccagttcatt    2640 gagatgtgtc tgatggtcac agctgatcac gggccagctc tctctggagc cataacaccc   2700
atcatctgtg ctcgggctgg gaaggacctg gtctccagcc tcacctcagg gctgctcacc   2760
```

-continued

```
attggagacc ggtttggggg tgccttggat gccgcagcaa agatgttcag taaagccttt    2820
gacagcggca tcattcccat ggagttcgtc aacaagatga agaaggaggg gaagctgatc    2880
atgggcatcg ccatcgagt aaaatcgata acaacccag acatgcgagt gcagatcctc     2940
aaggacttcg tcaaacagca cttccccgcc accccgctgc tcgactatgc cctggaagtg    3000
gagaagatta ccacctccaa gaagccaaat cttatcctga atgtggacgg cttcatcggc    3060
gttgcgtttg tggacatgct caggaactgt ggctccttca cccggaggag agctgatgaa    3120
tatgttgaca ttggagccct caatggcatc tttgtgctag aaggagtat gggcttcatt    3180 gggcactacc ttgaccagaa gaggctgaag caagggctgt atcgtcaccc ctgggatgac    3240
atttcctatg ttcttccaga acacatgagc atgtaa                              3276
```

<210> SEQ ID NO 31
<211> LENGTH: 549
<212> TYPE: PRT
<213> ORGANISM: S. cerevisiae

<400> SEQUENCE: 31

```
Met Ser Pro Ser Lys Met Asn Ala Thr Val Gly Ser Thr Ser Glu Val
  1               5                  10                  15

Glu Gln Lys Ile Arg Gln Glu Leu Ala Leu Ser Asp Glu Val Thr Thr
             20                  25                  30

Ile Arg Arg Asn Ala Pro Ala Val Leu Tyr Glu Asp Gly Leu Lys
         35                  40                  45

Glu Asn Lys Thr Val Ile Ser Ser Gly Ala Leu Ile Ala Tyr Ser
     50                  55                  60

Gly Val Lys Thr Gly Arg Ser Pro Lys Asp Lys Arg Ile Val Glu Glu
 65                  70                  75                  80

Pro Thr Ser Lys Asp Glu Ile Trp Trp Gly Pro Val Asn Lys Pro Cys
                 85                  90                  95

Ser Glu Arg Thr Trp Ser Ile Asn Arg Glu Arg Ala Ala Asp Tyr Leu
            100                 105                 110

Arg Thr Arg Asp His Ile Tyr Ile Val Asp Ala Phe Ala Gly Trp Asp
        115                 120                 125

Pro Lys Tyr Arg Ile Lys Val Arg Val Cys Ala Arg Ala Tyr His
    130                 135                 140

Ala Leu Phe Met Thr Asn Met Leu Ile Arg Pro Thr Glu Glu Leu
145                 150                 155                 160

Ala His Phe Gly Glu Pro Asp Phe Thr Val Trp Asn Ala Gly Gln Phe
                165                 170                 175

Pro Ala Asn Leu His Thr Gln Asp Met Ser Ser Lys Ser Thr Ile Glu
            180                 185                 190

Ile Asn Phe Lys Ala Met Glu Met Ile Ile Leu Gly Thr Glu Tyr Ala
        195                 200                 205

Gly Glu Met Lys Lys Gly Ile Phe Thr Val Met Phe Tyr Leu Met Pro
    210                 215                 220

Val His His Asn Val Leu Thr Leu His Ser Ser Ala Asn Gln Gly Ile
225                 230                 235                 240

Gln Asn Gly Asp Val Thr Leu Phe Phe Gly Leu Ser Gly Thr Gly Lys
                245                 250                 255

Thr Thr Leu Ser Ala Asp Pro His Arg Leu Leu Ile Gly Asp Asp Glu
            260                 265                 270

His Cys Trp Ser Asp His Gly Val Phe Asn Ile Glu Gly Gly Cys Tyr
```

```
            275                 280                 285
Ala Lys Cys Ile Asn Leu Ser Ala Glu Lys Glu Pro Glu Ile Phe Asp
    290                 295                 300
Ala Ile Lys Phe Gly Ser Val Leu Glu Asn Val Ile Tyr Asp Glu Lys
305                 310                 315                 320
Ser His Val Val Asp Tyr Asp Ser Ser Ile Thr Glu Asn Thr Arg
                325                 330                 335
Cys Ala Tyr Pro Ile Asp Tyr Ile Pro Ser Ala Lys Ile Pro Cys Leu
            340                 345                 350
Ala Asp Ser His Pro Lys Asn Ile Ile Leu Leu Thr Cys Asp Ala Ser
        355                 360                 365
Gly Val Leu Pro Pro Val Ser Lys Leu Thr Pro Glu Gln Val Met Tyr
    370                 375                 380
His Phe Ile Ser Gly Tyr Thr Ser Lys Met Ala Gly Thr Glu Gln Gly
385                 390                 395                 400
Val Thr Glu Pro Glu Pro Thr Phe Ser Ser Cys Phe Gly Gln Pro Phe
                405                 410                 415
Leu Ala Leu His Pro Ile Arg Tyr Ala Thr Met Leu Ala Thr Lys Met
            420                 425                 430
Ser Gln His Lys Ala Asn Ala Tyr Leu Ile Asn Thr Gly Trp Thr Gly
        435                 440                 445
Ser Ser Tyr Val Ser Gly Gly Lys Arg Cys Pro Leu Lys Tyr Thr Arg
    450                 455                 460
Ala Ile Leu Asp Ser Ile His Asp Gly Ser Leu Ala Asn Glu Thr Tyr
465                 470                 475                 480
Glu Thr Leu Pro Ile Phe Asn Leu Gln Val Pro Thr Lys Val Asn Gly
                485                 490                 495
Val Pro Ala Glu Leu Leu Asn Pro Ala Lys Asn Trp Ser Gln Gly Glu
            500                 505                 510
Ser Lys Tyr Arg Gly Ala Val Thr Asn Leu Ala Asn Leu Phe Val Gln
        515                 520                 525
Asn Phe Lys Ile Tyr Gln Asp Arg Ala Thr Pro Asp Val Leu Ala Ala
    530                 535                 540
Gly Pro Gln Phe Glu
545

<210> SEQ ID NO 32
<211> LENGTH: 1650
<212> TYPE: DNA
<213> ORGANISM: S. cerevisiae
<220> FEATURE:
<221> NAME/KEY: gene
<222> LOCATION: (1)..(1650)
<223> OTHER INFORMATION: PCK1 (SGD, YKR097W)

<400> SEQUENCE: 32
atgtcccctt ctaaaatgaa tgctacagta ggatctactt ccgaagttga acaaaaaatc      60
agacaagaat tggctcttag tgacgaagtc accaccatca gacgcaatgc tccagctgcc     120
gttttgtatg aagatggtct aaaagaaaat aaaactgtca tttcatcaag cggtgcattg     180
atcgcttatt ccggtgttaa aaccggaaga tctccaaagg acaaacgtat tgttgaagaa     240
cctacctcga agacgaaat ttggtggggt ccggtcaata accatgttc tgaaagaaca     300 tggtctatca accgtgaaag agctgcagat tacttgagaa caagagacca catttatatt     360
gtcgatgcat tgcaggatgg gatccaaaaa tacagaatca aagtccgcgt tgtttgtgcc     420
```

```
agggcttacc acgctttatt catgacaaat atgcttatta gacctacaga agaagaatta    480
gcccattttg gagaacctga ttttactgtc tggaacgctg gtcagttccc agccaattta    540
cacacccagg atatgtcttc aaagagtact atagaaatta acttcaaagc aatggaaatg    600
atcattttag gtaccgaata cgccggtgaa atgaaaaaag gtattttcac agttatgttt    660
tacttgatgc ctgtgcacca taacgtttta actttgcact cttccgccaa ccagggtatt    720
caaaacggtg acgttacttt attctttggc ctaagtggta ccgggaaaac cactttatcc    780
gcagacccac atagattgtt gatcggcgat gatgaacatt gttggtccga ccatggtgtc    840
ttcaatatcg aaggtggttg ttacgccaag tgtattaatt tatctgccga aaaggagcct    900
gaaattttcg acgctatcaa gtttggttct gtattagaaa acgttatcta tgacgagaag    960
tcgcatgtag tcgactatga cgactcttct attactgaaa atactagatg tgcctaccca   1020
attgactaca ttccaagtgc caagattcca tgtttggcgg actctcatcc aaagaacatt   1080
atcctgctaa cttgtgatgc ttcgggtgtt ttaccaccag tatctaaatt gactcctgaa   1140
caagtcatgt accatttcat ctctggttac acttctaaaa tggctggtac tgagcaaggt   1200
gtcactgaac ctgaaccaac attttcatct tgtttcggac aacccttcct agccttgcac   1260
cctattagat acgcaaccat gttagctaca agatgtctc aacataaagc taatgcgtac   1320
ttaatcaaca ccggctggac tggttcttcc tacgtatctg gtggtaaacg ttgcccattg   1380
aagtacacaa gggccattct ggattctatt catgatggtt cgttagccaa tgaaacgtac   1440
gaaactttac cgattttcaa tcttcaagta cctaccaagg ttaacggtgt tccagctgag   1500
cttttgaatc ctgctaaaaa ctggtctcaa ggtgaatcca atacagagg tgcagttacc   1560
aacttggcca acttgtttgt tcaaaatttc aagatttatc aagacagagc cacaccagat   1620
gtattagccg ctggtcctca attcgagtaa                                    1650
```

<210> SEQ ID NO 33
<211> LENGTH: 506
<212> TYPE: PRT
<213> ORGANISM: S. cerevisiae

<400> SEQUENCE: 33

```
Met Pro Glu Ser Arg Leu Gln Arg Leu Ala Asn Leu Lys Ile Gly Thr
  1               5                  10                  15

Pro Gln Gln Leu Arg Arg Thr Ser Ile Ile Gly Thr Ile Gly Pro Lys
                 20                  25                  30

Thr Asn Ser Cys Glu Ala Ile Thr Ala Leu Arg Lys Ala Gly Leu Asn
             35                  40                  45

Ile Ile Arg Leu Asn Phe Ser His Gly Ser Tyr Glu Phe His Gln Ser
         50                  55                  60

Val Ile Glu Asn Ala Val Lys Ser Glu Gln Gln Phe Pro Gly Arg Pro
 65                  70                  75                  80

Leu Ala Ile Ala Leu Asp Thr Lys Gly Pro Glu Ile Arg Thr Gly Arg
                 85                  90                  95

Thr Leu Asn Asp Gln Asp Leu Tyr Ile Pro Val Asp His Gln Met Ile
            100                 105                 110

Phe Thr Thr Asp Ala Ser Phe Ala Asn Thr Ser Asn Asp Lys Ile Met
        115                 120                 125

Tyr Ile Asp Tyr Ala Asn Leu Thr Lys Val Ile Val Pro Gly Arg Phe
    130                 135                 140

Ile Tyr Val Asp Asp Gly Ile Leu Ser Phe Lys Val Leu Gln Ile Ile
145                 150                 155                 160
```

Asp Glu Ser Asn Leu Arg Val Gln Ala Val Asn Ser Gly Tyr Ile Ala
            165                 170                 175

Ser His Lys Gly Val Asn Leu Pro Asn Thr Asp Val Asp Leu Pro Pro
        180                 185                 190

Leu Ser Ala Lys Asp Met Lys Asp Leu Gln Phe Gly Val Arg Asn Gly
        195                 200                 205

Ile His Ile Val Phe Ala Ser Phe Ile Arg Thr Ser Glu Asp Val Leu
    210                 215                 220

Ser Ile Arg Lys Ala Leu Gly Ser Glu Gly Gln Asp Ile Lys Ile Ile
225                 230                 235                 240

Ser Lys Ile Glu Asn Gln Gln Gly Leu Asp Asn Phe Asp Glu Ile Leu
                245                 250                 255

Glu Val Thr Asp Gly Val Met Ile Ala Arg Gly Asp Leu Gly Ile Glu
            260                 265                 270

Ile Leu Ala Pro Glu Val Leu Ala Ile Gln Lys Lys Leu Ile Ala Lys
        275                 280                 285

Cys Asn Leu Ala Gly Lys Pro Val Ile Cys Ala Thr Gln Met Leu Asp
        290                 295                 300

Ser Met Thr His Asn Pro Arg Pro Thr Arg Ala Glu Val Ser Asp Val
305                 310                 315                 320

Gly Asn Ala Val Leu Asp Gly Ala Asp Cys Val Met Leu Ser Gly Glu
                325                 330                 335

Thr Ala Lys Gly Asp Tyr Pro Val Asn Ala Val Asn Ile Met Ala Ala
            340                 345                 350

Thr Ala Leu Ile Ala Glu Ser Thr Ile Ala His Leu Ala Leu Tyr Asp
        355                 360                 365

Asp Leu Arg Asp Ala Thr Pro Lys Pro Thr Ser Thr Thr Glu Thr Val
    370                 375                 380

Ala Ala Ala Ala Thr Ala Ala Ile Leu Glu Gln Asp Gly Lys Ala Ile
385                 390                 395                 400

Val Val Leu Ser Thr Thr Gly Asn Thr Ala Arg Leu Leu Ser Lys Tyr
                405                 410                 415

Arg Pro Ser Cys Pro Ile Ile Leu Val Thr Arg His Ala Arg Thr Ala
            420                 425                 430

Arg Ile Ala His Leu Tyr Arg Gly Val Phe Pro Phe Leu Tyr Glu Pro
        435                 440                 445

Lys Arg Leu Asp Asp Trp Gly Glu Asp Val His Arg Arg Leu Lys Phe
    450                 455                 460

Gly Val Glu Met Ala Arg Ser Phe Gly Met Val Asp Asn Gly Asp Thr
465                 470                 475                 480

Val Val Ser Ile Gln Gly Phe Lys Gly Gly Val Gly His Ser Asn Thr
                485                 490                 495

Leu Arg Ile Ser Thr Val Gly Gln Glu Phe
            500                 505

<210> SEQ ID NO 34
<211> LENGTH: 1521
<212> TYPE: DNA
<213> ORGANISM: S. cerevisiae
<220> FEATURE:
<221> NAME/KEY: gene
<222> LOCATION: (1)..(1521)
<223> OTHER INFORMATION: PYK2 (SGD, YOR347C)

<400> SEQUENCE: 34

```
atgccagagt ccagattgca gagactagct aatttgaaaa taggaactcc gcagcagctc    60
agacgcacct ccataatagg taccattggg cccaagacaa atagctgcga ggccattact   120
gctctgagaa aagctggttt gaacatcatt cgattgaact tttcccatgg ctcctacgaa   180
ttccatcaat cagtaatcga aaatgctgtg aaatcggaac agcaattccc tggcaggccg   240
ctcgccattg ccctggatac caagggtccc gagatcagaa caggtcgcac gttaaatgac   300
caagatcttt atatcccgt agaccaccaa atgatcttta ccactgacgc aagttttgca   360
aacacctcca atgataaaat catgtatata gactatgcta acctgacaaa agttatcgtt   420
ccggggagat ttatatacgt ggacgacggg attctctctt ttaaagtgct ccaaatcatt   480
gacgaatcta atttaagggt gcaagcggta aactcgggtt atatcgcatc tcataaaggt   540
gttaatctgc ctaataccga cgttgatttg ccccccttgt ccgccaaaga catgaaggac   600
ttgcaattcg gagtccgcaa tggcattcac atcgtatttg cctctttcat aagaacttca   660
gaagatgtgt tgtctatcag aaaagcgttg ggttctgaag gcaagatat caagattata   720
tccaagatag aaaaccagca agggttggat aattttgacg aaatcctgga agtcacggat   780
ggtgttatga tagcgagagg cgatttagga attgaaatcc tggcacctga agtattagcc   840
attcaaaaaa agctgattgc aaaatgtaat ttggcgggca aacctgtcat ttgcgcgact   900
cagatgctgg attcaatgac acacaatccg agaccgacaa gggctgaagt atcggatgtg   960
ggtaacgctg tgttggatgg tgctgattgt gttatgcttt ctggagaaac ggcgaagggt  1020
gattatccgg tgaatgcagt taatattatg gcggcgaccg ctctgattgc tgaaagtact  1080
atcgctcatt tggctctttta tgacgatctc agagacgcca ctcccaaacc tacttccact  1140
acggaaactg tagcagctgc agctaccgca gcaatcttgg agcaagatgg taaggccatc  1200
gttgtattat ctactacagg gaacacggca aggctactgt cgaagtatag accaagctgc  1260
cctatcatat tagtaacaag acacgcaaga acggcaagaa ttgcgcattt gtatagaggt  1320
gttttcccat ttctgtatga accgaaacgc ctagacgact ggggtgagga tgttcatagg  1380
cgcctaaagt ttggtgttga atggcgagg tctttcggaa tggtggacaa cggtgatact  1440
gttgtttcca ttcaaggatt caaggagga gtcggccatt ccaataccit acgcatttct  1500
actgttggtc aagaattcta g                                             1521
```

<210> SEQ ID NO 35
<211> LENGTH: 377
<212> TYPE: PRT
<213> ORGANISM: S. cerevisiae

<400> SEQUENCE: 35

```
Met Pro His Ser Val Thr Pro Ser Ile Glu Gln Asp Ser Leu Lys Ile
  1               5                  10                  15

Ala Ile Leu Gly Ala Ala Gly Gly Ile Gly Gln Ser Leu Ser Leu Leu
             20                  25                  30

Leu Lys Ala Gln Leu Gln Tyr Gln Leu Lys Glu Ser Asn Arg Ser Val
         35                  40                  45

Thr His Ile His Leu Ala Leu Tyr Asp Val Asn Gln Glu Ala Ile Asn
     50                  55                  60

Gly Val Thr Ala Asp Leu Ser His Ile Asp Thr Pro Ile Ser Val Ser
 65                  70                  75                  80

Ser His Ser Pro Ala Gly Gly Ile Glu Asn Cys Leu His Asn Ala Ser
                 85                  90                  95

Ile Val Val Ile Pro Ala Gly Val Pro Arg Lys Pro Gly Met Thr Arg
```

| | | | | 100 | | | | 105 | | | | 110 | |
|---|---|---|---|---|---|---|---|---|---|---|---|---|---|
| Asp | Asp | Leu | Phe | Asn | Val | Asn | Ala | Gly | Ile | Ile | Ser | Gln | Leu | Gly | Asp |
| | | | | 115 | | | | | 120 | | | | 125 | |

Ser Ile Ala Glu Cys Cys Asp Leu Ser Lys Val Phe Val Leu Val Ile
    130                 135                 140

Ser Asn Pro Val Asn Ser Leu Val Pro Val Met Val Ser Asn Ile Leu
145                 150                 155                 160

Lys Asn His Pro Gln Ser Arg Asn Ser Gly Ile Glu Arg Arg Ile Met
            165                 170                 175

Gly Val Thr Lys Leu Asp Ile Val Arg Ala Ser Thr Phe Leu Arg Glu
        180                 185                 190

Ile Asn Ile Glu Ser Gly Leu Thr Pro Arg Val Asn Ser Met Pro Asp
            195                 200                 205

Val Pro Val Ile Gly Gly His Ser Gly Glu Thr Ile Ile Pro Leu Phe
    210                 215                 220

Ser Gln Ser Asn Phe Leu Ser Arg Leu Asn Glu Asp Gln Leu Lys Tyr
225                 230                 235                 240

Leu Ile His Arg Val Gln Tyr Gly Gly Asp Glu Val Val Lys Ala Lys
            245                 250                 255

Asn Gly Lys Gly Ser Ala Thr Leu Ser Met Ala His Ala Gly Tyr Lys
        260                 265                 270

Cys Val Val Gln Phe Val Ser Leu Leu Gly Asn Ile Glu Gln Ile
    275                 280                 285

His Gly Thr Tyr Tyr Val Pro Leu Lys Asp Ala Asn Asn Phe Pro Ile
            290                 295                 300

Ala Pro Gly Ala Asp Gln Leu Leu Pro Leu Val Asp Gly Ala Asp Tyr
305                 310                 315                 320

Phe Ala Ile Pro Leu Thr Ile Thr Thr Lys Gly Val Ser Tyr Val Asp
            325                 330                 335

Tyr Asp Ile Val Asn Arg Met Asn Asp Met Glu Arg Asn Gln Met Leu
        340                 345                 350

Pro Ile Cys Val Ser Gln Leu Lys Lys Asn Ile Asp Lys Gly Leu Glu
            355                 360                 365

Phe Val Ala Ser Arg Ser Ala Ser Ser
        370                 375

<210> SEQ ID NO 36
<211> LENGTH: 1134
<212> TYPE: DNA
<213> ORGANISM: S. cerevisiae
<220> FEATURE:
<221> NAME/KEY: gene
<222> LOCATION: (1)..(1134)
<223> OTHER INFORMATION: MDH2 (SGD YOL126C)

<400> SEQUENCE: 36

```
atgcctcact cagttacacc atccatagaa caagattcgt taaaaattgc cattttaggt    60
gctgccggtg gtatcgggca gtcgttatcg ctgcttttga aagctcagtt gcaataccag   120
ttaaaggaga gcaaccggag cgttacccac attcatctgg ctctttacga tgtcaaccaa   180
gaagccatca acggtgttac cgccgacttg tctcatatag acaccccat tccgtgtcg    240
agccactctc ctgcaggtgg cattgagaac tgtttgcata cgcttctat gttgtcatt    300
cctgcaggtt ttccaagaaa acctggcatg actcgtgatg acttatttaa cgtgaatgct   360
ggtatcatta gccagctcgg tgattctatt gcagaatgtt gtgatctttc caaggtcttc   420
```

```
gttcttgtca tttccaaccc tgttaattct ttagtcccag tgatggtttc taacattctt    480
aagaaccatc ctcagtctag aaattccggc attgaaagaa ggatcatggg tgtcaccaag    540
ctcgacattg tcagagcgtc cacttttcta cgtgagataa acattgagtc agggctaact    600
cctcgtgtta actccatgcc tgacgtccct gtaattggcg ggcattctgg cgagactatt    660
attccgttgt tttcacagtc aaacttccta tcgagattaa atgaggatca attgaaatat    720
ttaatacata gagtccaata cggtggtgat gaagtggtca aggccaagaa cggtaaaggt    780
agtgctacct tatcgatggc ccatgccggt tataagtgtg ttgtccaatt tgtttctttg    840
ttattgggta acattgagca gatccatgga acctactatg tgccattaaa agatgcgaac    900
aacttcccca ttgctcctgg ggcagatcaa ttattgcctc tggtggacgg tgcagactac    960
tttgccatac cattaactat tactacaaag ggtgtttcct atgtggatta tgacatcgtt   1020
aataggatga acgacatgga acgcaaccaa atgttgccaa tttgcgtctc ccagttaaag   1080
aaaaatatcg ataagggctt ggaattcgtt gcatcgagat ctgcatcatc ttaa         1134

<210> SEQ ID NO 37
<211> LENGTH: 669
<212> TYPE: PRT
<213> ORGANISM: S. cerevisiae

<400> SEQUENCE: 37

Met Leu Arg Thr Arg Leu Ser Val Ser Val Ala Ala Arg Ser Gln Leu
  1               5                  10                  15

Thr Arg Ser Leu Thr Ala Ser Arg Thr Ala Pro Leu Arg Arg Trp Pro
                 20                  25                  30

Ile Gln Gln Ser Arg Leu Tyr Ser Ser Asn Thr Arg Ser His Lys Ala
             35                  40                  45

Thr Thr Thr Arg Glu Asn Thr Phe Gln Lys Pro Tyr Ser Asp Glu Glu
         50                  55                  60

Val Thr Lys Thr Pro Val Gly Ser Arg Ala Arg Lys Ile Phe Glu Ala
 65                  70                  75                  80

Pro His Pro His Ala Thr Arg Leu Thr Val Glu Gly Ala Ile Glu Cys
                 85                  90                  95

Pro Leu Glu Ser Phe Gln Leu Leu Asn Ser Pro Leu Phe Asn Lys Gly
            100                 105                 110

Ser Ala Phe Thr Gln Glu Glu Arg Glu Ala Phe Asn Leu Glu Ala Leu
        115                 120                 125

Leu Pro Pro Gln Val Asn Thr Leu Asp Glu Gln Leu Glu Arg Ser Tyr
    130                 135                 140

Lys Gln Leu Cys Tyr Leu Lys Thr Pro Leu Ala Lys Asn Asp Phe Met
145                 150                 155                 160

Thr Ser Leu Arg Val Gln Asn Lys Val Leu Tyr Phe Ala Leu Ile Arg
                165                 170                 175

Arg His Ile Lys Glu Leu Val Pro Ile Ile Tyr Thr Pro Thr Glu Gly
            180                 185                 190

Asp Ala Ile Ala Ala Tyr Ser His Arg Phe Arg Lys Pro Glu Gly Val
        195                 200                 205

Phe Leu Asp Ile Thr Glu Pro Asp Ser Ile Glu Cys Arg Leu Ala Thr
    210                 215                 220

Tyr Gly Gly Asp Lys Asp Val Asp Tyr Ile Val Val Ser Asp Ser Glu
225                 230                 235                 240

Gly Ile Leu Gly Ile Gly Asp Gln Gly Ile Gly Gly Val Arg Ile Ala
                245                 250                 255
```

```
Ile Ser Lys Leu Ala Leu Met Thr Leu Cys Gly Gly Ile His Pro Gly
            260                 265                 270

Arg Val Leu Pro Val Cys Leu Asp Val Gly Thr Asn Asn Lys Lys Leu
            275                 280                 285

Ala Arg Asp Glu Leu Tyr Met Gly Asn Lys Phe Ser Arg Ile Arg Gly
290                 295                 300

Lys Gln Tyr Asp Asp Phe Leu Glu Lys Phe Ile Lys Ala Val Lys Lys
305                 310                 315                 320

Val Tyr Pro Ser Ala Val Leu His Phe Glu Asp Phe Gly Val Lys Asn
                325                 330                 335

Ala Arg Arg Leu Leu Glu Lys Tyr Arg Tyr Glu Leu Pro Ser Phe Asn
            340                 345                 350

Asp Asp Ile Gln Gly Thr Gly Ala Val Val Met Ala Ser Leu Ile Ala
            355                 360                 365

Ala Leu Lys His Thr Asn Arg Asp Leu Lys Asp Thr Arg Val Leu Ile
            370                 375                 380

Tyr Gly Ala Gly Ser Ala Gly Leu Gly Ile Ala Asp Gln Ile Val Asn
385                 390                 395                 400

His Met Val Thr His Gly Val Asp Lys Glu Ala Arg Lys Lys Ile
                405                 410                 415

Phe Leu Met Asp Arg Arg Gly Leu Ile Leu Gln Ser Tyr Glu Ala Asn
            420                 425                 430

Ser Thr Pro Ala Gln His Val Tyr Ala Lys Ser Asp Ala Glu Trp Ala
            435                 440                 445

Gly Ile Asn Thr Arg Ser Leu His Asp Val Val Glu Asn Val Lys Pro
            450                 455                 460

Thr Cys Leu Val Gly Cys Ser Thr Gln Ala Gly Ala Phe Thr Gln Asp
465                 470                 475                 480

Val Val Glu Glu Met His Lys His Asn Pro Arg Pro Ile Ile Phe Pro
                485                 490                 495

Leu Ser Asn Pro Thr Arg Leu His Glu Ala Val Pro Ala Asp Leu Met
            500                 505                 510

Lys Trp Thr Asn Asn Asn Ala Leu Val Ala Thr Gly Ser Pro Phe Pro
            515                 520                 525

Pro Val Asp Gly Tyr Arg Ile Ser Glu Asn Asn Asn Cys Tyr Ser Phe
            530                 535                 540

Pro Gly Ile Gly Leu Gly Ala Val Leu Ser Arg Ala Thr Thr Ile Thr
545                 550                 555                 560

Asp Lys Met Ile Ser Ala Ala Val Asp Gln Leu Ala Glu Leu Ser Pro
                565                 570                 575

Leu Arg Glu Gly Asp Ser Arg Pro Gly Leu Leu Pro Gly Leu Asp Thr
            580                 585                 590

Ile Thr Asn Thr Ser Ala Arg Leu Ala Thr Ala Val Ile Leu Gln Ala
            595                 600                 605

Leu Glu Glu Gly Thr Ala Arg Ile Glu Gln Glu Gln Val Pro Gly Gly
            610                 615                 620

Ala Pro Gly Glu Thr Val Lys Val Pro Arg Asp Phe Asp Glu Cys Leu
625                 630                 635                 640

Gln Trp Val Lys Ala Gln Met Trp Glu Pro Val Tyr Arg Pro Met Ile
                645                 650                 655

Lys Val Gln His Asp Pro Ser Val His Thr Asn Gln Leu
            660                 665
```

<210> SEQ ID NO 38
<211> LENGTH: 2010
<212> TYPE: DNA
<213> ORGANISM: S. cerevisiae
<220> FEATURE:
<221> NAME/KEY: gene
<222> LOCATION: (1)..(2010)
<223> OTHER INFORMATION: MAE1 (SGD YKL029C)

<400> SEQUENCE: 38

```
atgcttagaa ccagactatc cgtttccgtt gctgctagat cgcaactaac cagatccttg      60
acagcatcaa ggacagcacc attaagaaga tggcctattc agcaatcgcg tttatattct     120
tctaacacta gatcgcataa agctaccaca acaagagaaa atactttcca aaagccatac     180
agcgacgagg aggtcactaa acacccgtc ggttctcgcg ccagaaagat cttcgaagct      240
cctcacccac atgccactcg tttgactgta gaaggtgcca tagaatgtcc cttggagagc     300
tttcaacttt taaactctcc tttatttaac aagggttctg catttacaca agaagaaagg     360
gaagcgttta atttagaagc attgctacca ccacaagtga acactttgga cgaacaactg     420
gaaagaagct acaagcagtt atgctatttg aagacgccct tggccaaaaa cgacttcatg     480
acgtctttga gagtacagaa caaagtccta tattttgcat taataaggag acatatcaag     540
gaattagttc ctatcattta caccccaacc gaaggtgatg ctattgctgc ctattcccac     600
aggttcagaa agccagaagg tgtgttttta gacattaccg aacctgattc catcgaatgt     660
agattggcta catacggtgg agacaaagat gtagactaca tcgttgtgtc ggattcggaa     720
ggtattctgg gaattggtga ccaaggtatc ggtggtgtac gtattgctat ctccaaattg     780
gcattgatga cgctgtgcgg tggtattcat cccggccgtg tgctacctgt gtgtttggac     840
gtcggtacta caacaagaa actagcccgt gacgaattgt acatgggtaa caagttctcc     900
agaatcaggg gtaagcaata tgacgacttc ttggaaaaat tcatcaaggc cgttaagaaa     960
gtgtatccaa cgccgttct gcatttcgaa gatttcggtg ttaagaacgc tagaagatta    1020
ctagaaaagt acaggtacga attgccatca ttcaacgatg acattcaggg caccggtgcc    1080
gtcgtgatgg cctcgttgat tgctgctttg aaacatacca acagagactt gaaagacacc    1140
agagtgctta tttacggtgc cgggtctgcg ggcctcggta tcgcagatca aattgtgaat    1200
catatggtca cgcacggcgt tgacaaggaa gaagcgcgca agaaaatctt cttgatggac    1260
agacgtgggt taattctaca atcttacgag gctaactcca ctcccgccca acacgtatac    1320
gctaagagtg atgcggaatg ggctggtatc aacacccgct ctttacatga tgtggtggag    1380
aacgtcaaac caacgtgttt ggttggctgc tccacacaag caggcgcatt cactcaagat    1440
gtcgtagaag aaatgcacaa gcacaatcct agaccgatca ttttcccatt atccaaccct    1500
actagactac acgaagccgt tcctgccgat ttaatgaagt ggaccaacaa caacgctctt    1560
gtagctaccg gatctccttt cccacctgtt gatggttacc gtatctcgga gaacaacaat    1620
tgttactctt tcccaggtat cggtttaggt gccgtactat cgcgtgccac caccatcaca    1680
gacaagatga tctccgctgc agtggaccaa ctagccgaat tgtcgccact aagagagggc    1740
gactcgagac ctgggttgct acccggcctg gacaccatca ccaacacttc tgcgcgtcta    1800
gctaccgctg tgatcttgca agcactcgag gagggaaccg cccgtatcga gcaagaacaa    1860
gtaccgggag gagctcccgg cgaaactgtc aaggttcctc gtgactttga cgaatgttta    1920
cagtgggtca agcccaaat gtgggagcct gtgtacagac ctatgatcaa ggtccaacat    1980
gacccatcgg tgcacaccaa ccaattgtag                                      2010
```

<210> SEQ ID NO 39
<211> LENGTH: 563
<212> TYPE: PRT
<213> ORGANISM: S. cerevisiae

<400> SEQUENCE: 39

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
    210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
        355                 360                 365

Trp Met Trp Asn Gln Leu Gly Asn Phe Leu Gln Glu Gly Asp Val Val

```
                370              375               380
Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
                420                 425                 430

Asp Pro Lys Lys Arg Val Ile Leu Phe Ile Gly Asp Gly Ser Leu Gln
                435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
                500                 505                 510

Ala Thr Thr Gly Glu Trp Asp Lys Leu Thr Gln Asp Lys Ser Phe Asn
                515                 520                 525

Asp Asn Ser Lys Ile Arg Met Ile Glu Ile Met Leu Pro Val Phe Asp
530                 535                 540

Ala Pro Gln Asn Leu Val Glu Gln Ala Lys Leu Thr Ala Ala Thr Asn
545                 550                 555                 560

Ala Lys Gln
```

<210> SEQ ID NO 40
<211> LENGTH: 1692
<212> TYPE: DNA
<213> ORGANISM: S. cerevisiae
<220> FEATURE:
<221> NAME/KEY: gene
<222> LOCATION: (1)..(1692)
<223> OTHER INFORMATION: PDC1 (SGD YLR044C)

<400> SEQUENCE: 40

```
atgtctgaaa ttactttggg taaatatttg ttcgaaagat taaagcaagt caacgttaac        60
accgttttcg gtttgccagg tgacttcaac ttgtccttgt tggacaagat ctacgaagtt       120
gaaggtatga gatgggctgg taacgccaac gaattgaacg ctgcttacgc cgctgatggt       180
tacgctcgta tcaagggtat gtcttgtatc atcaccacct tcggtgtcgg tgaattgtct       240
gctttgaacg gtattgccgg ttcttacgct gaacacgtcg gtgttttgca cgttgttggt       300
gtcccatcca tctctgctca agctaagcaa ttgttgttgc accacacctt gggtaacggt       360
gacttcactg ttttccacag aatgtctgcc aacatttctg aaaccactgc tatgatcact       420
gacattgcta ccgccccagc tgaaattgac agatgtatca gaaccactta cgtcacccaa       480
agaccagtct acttaggttt gccagctaac ttggtcgact gaacgtccc agctaagttg       540
ttgcaaactc caattgacat gtctttgaag ccaaacgatg ctgaatccga aaggaagtc        600
attgacacca tcttggcttt ggtcaaggat gctaagaacc cagttatctt ggctgatgct       660
tgttgttcca gacacgacgt caaggctgaa actaagaagt tgattgactt gactcaattc       720
ccagctttcg tcacccccaat gggtaagggt tccattgacg aacaacaccc aagatacggt       780
ggtgtttacg tcggtaccct tgtccaagcca gaagttaagg aagccgttga atctgctgac       840
ttgattttgt ctgtcggtgc tttgttgtct gatttcaaca ccggttcttt ctcttactct       900
```

```
tacaagacca agaacattgt cgaattccac tccgaccaca tgaagatcag aaacgccact    960
ttcccaggtg tccaaatgaa attcgttttg caaaagttgt tgaccactat tgctgacgcc   1020
gctaagggtt acaagccagt tgctgtccca gctagaactc cagctaacgc tgctgtccca   1080
gcttctaccc cattgaagca agaatggatg tggaaccaat tgggtaactt cttgcaagaa   1140
ggtgatgttg tcattgctga aaccggtacc tccgctttcg gtatcaacca aaccactttc   1200
ccaaacaaca cctacggtat ctctcaagtc ttatggggtt ccattggttt caccactggt   1260
gctaccttgg gtgctgcttt cgctgctgaa gaaattgatc aaagaagag  agttatctta   1320
ttcattggtg acggttcttt gcaattgact gttcaagaaa tctccaccat gatcagatgg   1380
ggcttgaagc atacttgtt cgtcttgaac aacgatggtt acaccattga aaagttgatt   1440
cacggtccaa aggctcaata acgaaatt caaggttggg accacctatc cttgttgcca   1500
actttcggtg ctaaggacta tgaaacccac agagtcgcta ccaccggtga atgggacaag   1560
ttgacccaag acaagtcttt caacgacaac tctaagatca gaatgattga aatcatgttg   1620
ccagtcttcg atgctccaca aaacttggtt gaacaagcta agttgactgc tgctaccaac   1680
gctaagcaat aa                                                      1692

<210> SEQ ID NO 41
<211> LENGTH: 563
<212> TYPE: PRT
<213> ORGANISM: S. cerevisiae

<400> SEQUENCE: 41

Met Ser Glu Ile Thr Leu Gly Lys Tyr Leu Phe Glu Arg Leu Ser Gln
  1               5                  10                  15

Val Asn Cys Asn Thr Val Phe Gly Leu Pro Gly Asp Phe Asn Leu Ser
                 20                  25                  30

Leu Leu Asp Lys Leu Tyr Glu Val Lys Gly Met Arg Trp Ala Gly Asn
             35                  40                  45

Ala Asn Glu Leu Asn Ala Ala Tyr Ala Ala Asp Gly Tyr Ala Arg Ile
         50                  55                  60

Lys Gly Met Ser Cys Ile Ile Thr Thr Phe Gly Val Gly Glu Leu Ser
 65                  70                  75                  80

Ala Leu Asn Gly Ile Ala Gly Ser Tyr Ala Glu His Val Gly Val Leu
                 85                  90                  95

His Val Val Gly Val Pro Ser Ile Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Asn
    130                 135                 140

Ala Pro Ala Glu Ile Asp Arg Cys Ile Arg Thr Thr Tyr Thr Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Glu Thr Pro Ile Asp Leu Ser Leu Lys Pro Asn
            180                 185                 190

Asp Ala Glu Ala Glu Ala Val Arg Thr Val Val Glu Leu Ile
        195                 200                 205

Lys Asp Ala Lys Asn Pro Val Ile Leu Ala Asp Ala Cys Ala Ser Arg
    210                 215                 220

His Asp Val Lys Ala Glu Thr Lys Lys Leu Met Asp Leu Thr Gln Phe
```

-continued

```
                225                 230                 235                 240
        Pro Val Tyr Val Thr Pro Met Gly Lys Gly Ala Ile Asp Glu Gln His
                        245                 250                 255
        Pro Arg Tyr Gly Gly Val Tyr Val Gly Thr Leu Ser Arg Pro Glu Val
                        260                 265                 270
        Lys Lys Ala Val Glu Ser Ala Asp Leu Ile Leu Ser Ile Gly Ala Leu
                        275                 280                 285
        Leu Ser Asp Phe Asn Thr Gly Ser Phe Ser Tyr Ser Tyr Lys Thr Lys
                        290                 295                 300
        Asn Ile Val Glu Phe His Ser Asp His Ile Lys Ile Arg Asn Ala Thr
        305                 310                 315                 320
        Phe Pro Gly Val Gln Met Lys Phe Ala Leu Gln Lys Leu Leu Asp Ala
                        325                 330                 335
        Ile Pro Glu Val Val Lys Asp Tyr Lys Pro Val Ala Val Pro Ala Arg
                        340                 345                 350
        Val Pro Ile Thr Lys Ser Thr Pro Ala Asn Thr Pro Met Lys Gln Glu
                        355                 360                 365
        Trp Met Trp Asn His Leu Gly Asn Phe Leu Arg Glu Gly Asp Ile Val
                        370                 375                 380
        Ile Ala Glu Thr Gly Thr Ser Ala Phe Gly Ile Asn Gln Thr Thr Phe
        385                 390                 395                 400
        Pro Thr Asp Val Tyr Ala Ile Val Gln Val Leu Trp Gly Ser Ile Gly
                        405                 410                 415
        Phe Thr Val Gly Ala Leu Leu Gly Ala Thr Met Ala Ala Glu Glu Leu
                        420                 425                 430
        Asp Pro Lys Lys Arg Val Ile Leu Phe Ile Gly Asp Gly Ser Leu Gln
                        435                 440                 445
        Leu Thr Val Gln Glu Ile Ser Thr Met Ile Arg Trp Gly Leu Lys Pro
                        450                 455                 460
        Tyr Ile Phe Val Leu Asn Asn Asn Gly Tyr Thr Ile Glu Lys Leu Ile
        465                 470                 475                 480
        His Gly Pro His Ala Glu Tyr Asn Glu Ile Gln Gly Trp Asp His Leu
                        485                 490                 495
        Ala Leu Leu Pro Thr Phe Gly Ala Arg Asn Tyr Glu Thr His Arg Val
                        500                 505                 510
        Ala Thr Thr Gly Glu Trp Glu Lys Leu Thr Gln Asp Lys Asp Phe Gln
                        515                 520                 525
        Asp Asn Ser Lys Ile Arg Met Ile Glu Val Met Leu Pro Val Phe Asp
        530                 535                 540
        Ala Pro Gln Asn Leu Val Lys Gln Ala Gln Leu Thr Ala Ala Thr Asn
                        545                 550                 555                 560
        Ala Lys Gln

<210> SEQ ID NO 42
<211> LENGTH: 1692
<212> TYPE: DNA
<213> ORGANISM: S. cerevisiae
<220> FEATURE:
<221> NAME/KEY: gene
<222> LOCATION: (1)..(1692)
<223> OTHER INFORMATION: PDC5 (SGD YLR134W)

<400> SEQUENCE: 42
atgtctgaaa taaccttagg taaatatttta tttgaaagat tgagccaagt caactgtaac    60
accgtcttcg gtttgccagg tgactttaac ttgtctcttt tggataagct ttatgaagtc   120
```

```
aaaggtatga gatgggctgg taacgctaac gaattgaacg ctgcctatgc tgctgatggt    180
tacgctcgta tcaagggtat gtcctgtatt attaccacct tcggtgttgg tgaattgtct    240
gctttgaatg gtattgccgg ttcttacgct gaacatgtcg gtgttttgca cgttgttggt    300
gttccatcca tctcttctca agctaagcaa ttgttgttgc atcataccct gggtaacggt    360
gacttcactg ttttccacag aatgtctgcc aacatttctg aaaccactgc catgatcact    420
gatattgcta acgctccagc tgaaattgac agatgtatca gaaccaccta cactacccaa    480
agaccagtct acttgggttt gccagctaac ttggttgact gaacgtccc agccaagtta    540
ttggaaactc caattgactt gtcttttgaag ccaaacgacg ctgaagctga agctgaagtt    600
gttagaactg ttgttgaatt gatcaaggat gctaagaacc cagttatctt ggctgatgct    660
tgtgcttcta gacatgatgt caaggctgaa actaagaagt tgatggactt gactcaattc    720
ccagtttacg tcaccccaat gggtaagggt gctattgacg aacaacaccc aagatacggt    780
ggtgtttacg ttggtacctt gtctagacca gaagttaaga aggctgtaga atctgctgat    840
ttgatattgt ctatcggtgc tttgttgtct gatttcaata ccggttcttt ctcttactcc    900
tacaagacca aaaatatcgt tgaattccac tctgaccaca tcaagatcag aaacgccacc    960
ttcccaggtg ttcaaatgaa atttgccttg caaaaattgt tggatgctat tccagaagtc    1020
gtcaaggact acaaacctgt tgctgtccca gctagagttc aattaccaa gtctactcca    1080
gctaacactc aatgaagca agaatggatg tggaaccatt tgggtaactt cttgagagaa    1140
ggtgatattg ttattgctga aaccggtact tccgccttcg gtattaacca aactactttc    1200
ccaacagatg tatacgctat cgtccaagtc ttgtggggtt ccattggttt cacagtcggc    1260
gctctattgg gtgctactat ggccgctgaa gaacttgatc aaagaagag agttatttta    1320
ttcattggtg acggttctct acaattgact gttcaagaaa tctctaccat gattagatgg    1380
ggtttgaagc catacatttt tgtcttgaat aacaacggtt acaccattga aaaattgatt    1440
cacggtcctc atgccgaata taatgaaatt caaggttggg accacttggc cttattgcca    1500
acttttggtg ctagaaacta cgaaacccac agagttgcta ccactggtga atgggaaaag    1560
ttgactcaag acaaggactt ccaagacaac tctaagatta gaatgattga agttatgttg    1620
ccagtctttg atgctccaca aaacttggtt aaacaagctc aattgactgc cgctactaac    1680
gctaaacaat aa                                                         1692
```

<210> SEQ ID NO 43
<211> LENGTH: 563
<212> TYPE: PRT
<213> ORGANISM: S. cerevisiae

<400> SEQUENCE: 43

```
Met Ser Glu Ile Thr Leu Gly Lys Tyr Leu Phe Glu Arg Leu Lys Gln
 1               5                  10                  15

Val Asn Val Asn Thr Ile Phe Gly Leu Pro Gly Asp Phe Asn Leu Ser
            20                  25                  30

Leu Leu Asp Lys Ile Tyr Glu Val Asp Gly Leu Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Leu Ser Val Leu Val Thr Thr Phe Gly Val Gly Glu Leu Ser
65                  70                  75                  80

Ala Leu Asn Gly Ile Ala Gly Ser Tyr Ala Glu His Val Gly Val Leu
```

```
                        85                  90                  95
His Val Val Gly Val Pro Ser Ile Ser Ala Gln Ala Lys Gln Leu Leu
                100                 105                 110
Leu His His Thr Leu Gly Asn Gly Asp Phe Thr Val Phe His Arg Met
            115                 120                 125
Ser Ala Asn Ile Ser Glu Thr Thr Ser Met Ile Thr Asp Ile Ala Thr
        130                 135                 140
Ala Pro Ser Glu Ile Asp Arg Leu Ile Arg Thr Thr Phe Ile Thr Gln
145                 150                 155                 160
Arg Pro Ser Tyr Leu Gly Leu Pro Ala Asn Leu Val Asp Leu Lys Val
                165                 170                 175
Pro Gly Ser Leu Leu Glu Lys Pro Ile Asp Leu Ser Leu Lys Pro Asn
                180                 185                 190
Asp Pro Glu Ala Glu Lys Glu Val Ile Asp Thr Val Leu Glu Leu Ile
                195                 200                 205
Gln Asn Ser Lys Asn Pro Val Ile Leu Ser Asp Ala Cys Ala Ser Arg
        210                 215                 220
His Asn Val Lys Lys Glu Thr Gln Lys Leu Ile Asp Leu Thr Gln Phe
225                 230                 235                 240
Pro Ala Phe Val Thr Pro Leu Gly Lys Gly Ser Ile Asp Glu Gln His
                245                 250                 255
Pro Arg Tyr Gly Gly Val Tyr Val Gly Thr Leu Ser Lys Gln Asp Val
                260                 265                 270
Lys Gln Ala Val Glu Ser Ala Asp Leu Ile Leu Ser Val Gly Ala Leu
            275                 280                 285
Leu Ser Asp Phe Asn Thr Gly Ser Phe Ser Tyr Ser Tyr Lys Thr Lys
        290                 295                 300
Asn Val Val Glu Phe His Ser Asp Tyr Val Lys Val Lys Asn Ala Thr
305                 310                 315                 320
Phe Leu Gly Val Gln Met Lys Phe Ala Leu Gln Asn Leu Leu Lys Val
                325                 330                 335
Ile Pro Asp Val Val Lys Gly Tyr Lys Ser Val Pro Val Pro Thr Lys
                340                 345                 350
Thr Pro Ala Asn Lys Gly Val Pro Ala Ser Thr Pro Leu Lys Gln Glu
            355                 360                 365
Trp Leu Trp Asn Glu Leu Ser Lys Phe Leu Gln Glu Gly Asp Val Ile
        370                 375                 380
Ile Ser Glu Thr Gly Thr Ser Ala Phe Gly Ile Asn Gln Thr Ile Phe
385                 390                 395                 400
Pro Lys Asp Ala Tyr Gly Ile Ser Gln Val Leu Trp Gly Ser Ile Gly
                405                 410                 415
Phe Thr Thr Gly Ala Thr Leu Gly Ala Ala Phe Ala Ala Glu Glu Ile
                420                 425                 430
Asp Pro Asn Lys Arg Val Ile Leu Phe Ile Gly Asp Gly Ser Leu Gln
            435                 440                 445
Leu Thr Val Gln Glu Ile Ser Thr Met Ile Arg Trp Gly Leu Lys Pro
        450                 455                 460
Tyr Leu Phe Val Leu Asn Asn Asp Gly Tyr Thr Ile Glu Lys Leu Ile
465                 470                 475                 480
His Gly Pro His Ala Glu Tyr Asn Glu Ile Gln Thr Trp Asp His Leu
                485                 490                 495
Ala Leu Leu Pro Ala Phe Gly Ala Lys Lys Tyr Glu Asn His Lys Ile
                500                 505                 510
```

Ala Thr Thr Gly Glu Trp Asp Ala Leu Thr Thr Asp Ser Glu Phe Gln
    515                 520                 525

Lys Asn Ser Val Ile Arg Leu Ile Glu Leu Lys Leu Pro Val Phe Asp
    530                 535                 540

Ala Pro Glu Ser Leu Ile Lys Gln Ala Gln Leu Thr Ala Ala Thr Asn
545                 550                 555                 560

Ala Lys Gln

<210> SEQ ID NO 44
<211> LENGTH: 1692
<212> TYPE: DNA
<213> ORGANISM: S. cerevisiae
<220> FEATURE:
<221> NAME/KEY: gene
<222> LOCATION: (1)..(1692)
<223> OTHER INFORMATION: PDC6 (SGD YGR087C)

<400> SEQUENCE: 44

| | |
|---|---|
| atgtctgaaa ttactcttgg aaaatactta tttgaaagat tgaagcaagt taatgttaac | 60 |
| accatttttg ggctaccagg cgacttcaac ttgtccctat ggacaagat ttacgaggta | 120 |
| gatggattga gatgggctgg taatgcaaat gagctgaacg ccgcctatgc cgccgatggt | 180 |
| tacgcacgca tcaagggttt atctgtgctg gtaactactt ttggcgtagg tgaattatcc | 240 |
| gccttgaatg gtattgcagg atcgtatgca gaacacgtcg gtgtactgca tgttgttggt | 300 |
| gtcccctcta tctccgctca ggctaagcaa ttgttgttgc atcataccta gggtaacggt | 360 |
| gattttaccg ttttcacag aatgtccgcc aatatctcag aaactacatc aatgattaca | 420 |
| gacattgcta cagccccttc agaaatcgat aggttgatca ggacaacatt tataacacaa | 480 |
| aggcctagct acttggggtt gccagcgaat ttggtagatc taaaggttcc tggttctctt | 540 |
| ttggaaaaac cgattgatct atcattaaaa cctaacgatc ccgaagctga aaaggaagtt | 600 |
| attgataccg tactagaatt gatccagaat tcgaaaaacc ctgttatact atcggatgcc | 660 |
| tgtgcttcta ggcacaacgt taaaaagaa acccagaagt taattgattt gacgcaattc | 720 |
| ccagcttttg tgacacctct aggtaaaggg tcaatagatg aacagcatcc cagatatggc | 780 |
| ggtgtttatg tgggaacgct gtccaaacaa gacgtgaaac aggccgttga gtcggctgat | 840 |
| ttgatccttt cggtcggtgc tttgctctct gattttaaca caggttcgtt ttcctactcc | 900 |
| tacaagacta aaaatgtagt ggagtttcat tccgattacg taaaggtgaa gaacgctacg | 960 |
| ttcctcggtg tacaaatgaa atttgcacta caaaacttac tgaaggttat tcccgatgtt | 1020 |
| gttaagggct acaagagcgt tcccgtacca accaaaactc ccgcaaacaa aggtgtacct | 1080 |
| gctagcacgc ccttgaaaca agagtggttg tggaacgaat gtccaaatt cttgcaagaa | 1140 |
| ggtgatgtta tcatttccga gaccggcacg tctgccttcg gtatcaatca aactatcttt | 1200 |
| cctaaggacg cctacggtat ctcgcaggtg ttgtgggggt ccatcggttt tacaacagga | 1260 |
| gcaactttag gtgctgcctt tgccgctgag gagattgacc caacaagag agtcatctta | 1320 |
| ttcataggtg acgggtcttt gcagttaacc gtccaagaaa tctccaccat gatcagatgg | 1380 |
| gggttaaagc cgtatctttt tgtccttaac aacgacggct acactatcga aaagctgatt | 1440 |
| catgggcctc acgcagagta caacgaaatc cagacctggg atcacctcgc cctgttgccc | 1500 |
| gcatttggtg cgaaaaagta cgaaaatcac aagatcgcca ctacgggtga gtgggatgcc | 1560 |
| ttaaccactg attcagagtt ccagaaaaac tcggtgatca gactaattga actgaaactg | 1620 |
| cccgtctttg atgctccgga aagtttgatc aaacaagcgc aattgactgc cgctacaaat | 1680 | gccaaacaat aa                                                          1692

<210> SEQ ID NO 45
<211> LENGTH: 348
<212> TYPE: PRT
<213> ORGANISM: S. cerevisiae

<400> SEQUENCE: 45

Met Ser Ile Pro Glu Thr Gln Lys Gly Val Ile Phe Tyr Glu Ser His
  1               5                  10                  15

Gly Lys Leu Glu Tyr Lys Asp Ile Pro Val Pro Lys Pro Lys Ala Asn
             20                  25                  30

Glu Leu Leu Ile Asn Val Lys Tyr Ser Gly Val Cys His Thr Asp Leu
         35                  40                  45

His Ala Trp His Gly Asp Trp Pro Leu Pro Val Lys Leu Pro Leu Val
     50                  55                  60

Gly Gly His Glu Gly Ala Gly Val Val Val Gly Met Gly Glu Asn Val
 65                  70                  75                  80

Lys Gly Trp Lys Ile Gly Asp Tyr Ala Gly Ile Lys Trp Leu Asn Gly
                 85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Gln
        115                 120                 125

Tyr Ala Thr Ala Asp Ala Val Gln Ala Ala His Ile Pro Gln Gly Thr
    130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
        195                 200                 205

Glu Leu Phe Arg Ser Ile Gly Gly Glu Val Phe Ile Asp Phe Thr Lys
    210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Val Val Lys Ser
        275                 280                 285

Ile Ser Ile Val Gly Ser Tyr Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
                325                 330                 335

Gln Ile Val Gly Arg Tyr Val Val Asp Thr Ser Lys
            340                 345

<210> SEQ ID NO 46

<211> LENGTH: 1047
<212> TYPE: DNA
<213> ORGANISM: S. cerevisiae
<220> FEATURE:
<221> NAME/KEY: gene
<222> LOCATION: (1)..(1047)
<223> OTHER INFORMATION: ADH1 (SGD YOL086C)

<400> SEQUENCE: 46

```
atgtctatcc cagaaactca aaaggtgtt atcttctacg aatcccacgg taagttggaa      60
tacaaagata ttccagttcc aaagccaaag gccaacgaat gttgatcaa cgttaaatac    120
tctggtgtct gtcacactga cttgcacgct tggcacggtg actggccatt gccagttaag    180
ctaccattag tcggtggtca cgaaggtgcc ggtgtcgttg tcggcatggg tgaaaacgtt    240
aagggctgga gatcggtga ctacgccggt atcaaatggt tgaacggttc ttgtatggcc    300
tgtgaatact gtgaattggg taacgaatcc aactgtcctc acgctgactt gtctggttac    360
acccacgacg gttcttttcca acaatacgct accgctgacg ctgttcaagc cgctcacatt    420
cctcaaggta ccgacttggc ccaagtcgcc cccatcttgt gtgctggtat caccgtctac    480
aaggctttga gtctgctaa cttgatggcc ggtcactggg ttgctatctc cggtgctgct    540
ggtggtctag gttctttggc tgttcaatac gccaaggcta tgggttacag agtcttgggt    600
attgacggtg gtgaaggtaa ggaagaatta ttcagatcca tcggtggtga agtcttcatt    660
gacttcacta aggaaaagga cattgtcggt gctgttctaa aggccactga cggtggtgct    720
cacggtgtca tcaacgtttc cgtttccgaa gccgctattg aagcttctac cagatacgtt    780
agagctaacg gtaccaccgt tttggtcggt atgccagctg gtgccaagtg ttgttctgat    840
gtcttcaacc aagtcgtcaa gtccatctct attgttggtt cttacgtcgg taacagagct    900
gacaccagag aagctttgga cttcttcgcc agaggtttgg tcaagtctcc aatcaaggtt    960
gtcggcttgt ctaccttgcc agaaatttac gaaagatgg aaaagggtca atcgttggt    1020
agatacgttg ttgacacttc taaataa                                        1047
```

<210> SEQ ID NO 47
<211> LENGTH: 587
<212> TYPE: PRT
<213> ORGANISM: S. cerevisiae

<400> SEQUENCE: 47

```
Met Leu Trp Lys Arg Thr Cys Thr Arg Leu Ile Lys Pro Ile Ala Gln
1               5                   10                  15

Pro Arg Gly Arg Leu Val Arg Arg Ser Cys Tyr Arg Tyr Ala Ser Thr
            20                  25                  30

Gly Thr Gly Ser Thr Asp Ser Ser Ser Gln Trp Leu Lys Tyr Ser Val
        35                  40                  45

Ile Ala Ser Ser Ala Thr Leu Phe Gly Tyr Leu Phe Ala Lys Asn Leu
    50                  55                  60

Tyr Ser Arg Glu Thr Lys Glu Asp Leu Ile Glu Lys Leu Glu Met Val
65                  70                  75                  80

Lys Lys Ile Asp Pro Val Asn Ser Thr Leu Lys Leu Ser Ser Leu Asp
                85                  90                  95

Ser Pro Asp Tyr Leu His Asp Pro Val Lys Ile Asp Lys Val Val Glu
            100                 105                 110

Asp Leu Lys Gln Val Leu Gly Asn Lys Pro Glu Asn Tyr Ser Asp Ala
        115                 120                 125

Lys Ser Asp Leu Asp Ala His Ser Asp Thr Tyr Phe Asn Thr His His
```

```
            130                 135                 140
Pro Ser Pro Glu Gln Arg Pro Arg Ile Ile Leu Phe Pro His Thr Thr
145                 150                 155                 160

Glu Glu Val Ser Lys Ile Leu Lys Ile Cys His Asp Asn Asn Met Pro
                165                 170                 175

Val Val Pro Phe Ser Gly Gly Thr Ser Leu Glu Gly His Phe Leu Pro
            180                 185                 190

Thr Arg Ile Gly Asp Thr Ile Thr Val Asp Leu Ser Lys Phe Met Asn
        195                 200                 205

Asn Val Val Lys Phe Asp Lys Leu Asp Leu Asp Ile Thr Val Gln Ala
    210                 215                 220

Gly Leu Pro Trp Glu Asp Leu Asn Asp Tyr Leu Ser Asp His Gly Leu
225                 230                 235                 240

Met Phe Gly Cys Asp Pro Gly Pro Gly Ala Gln Ile Gly Gly Cys Ile
                245                 250                 255

Ala Asn Ser Cys Ser Gly Thr Asn Ala Tyr Arg Tyr Gly Thr Met Lys
                260                 265                 270

Glu Asn Ile Ile Asn Met Thr Ile Val Leu Pro Asp Gly Thr Ile Val
            275                 280                 285

Lys Thr Lys Lys Arg Pro Arg Lys Ser Ser Ala Gly Tyr Asn Leu Asn
290                 295                 300

Gly Leu Phe Val Gly Ser Glu Gly Thr Leu Gly Ile Val Thr Glu Ala
305                 310                 315                 320

Thr Val Lys Cys His Val Lys Pro Lys Ala Glu Thr Val Ala Val Val
                325                 330                 335

Ser Phe Asp Thr Ile Lys Asp Ala Ala Ala Cys Ala Ser Asn Leu Thr
            340                 345                 350

Gln Ser Gly Ile His Leu Asn Ala Met Glu Leu Leu Asp Glu Asn Met
        355                 360                 365

Met Lys Leu Ile Asn Ala Ser Glu Ser Thr Asp Arg Cys Asp Trp Val
    370                 375                 380

Glu Lys Pro Thr Met Phe Phe Lys Ile Gly Gly Arg Ser Pro Asn Ile
385                 390                 395                 400

Val Asn Ala Leu Val Asp Glu Val Lys Ala Val Ala Gln Leu Asn His
                405                 410                 415

Cys Asn Ser Phe Gln Phe Ala Lys Asp Asp Glu Lys Leu Glu Leu
                420                 425                 430

Trp Glu Ala Arg Lys Val Ala Leu Trp Ser Val Leu Asp Ala Asp Lys
            435                 440                 445

Ser Lys Asp Lys Ser Ala Lys Ile Trp Thr Thr Asp Val Ala Val Pro
        450                 455                 460

Val Ser Gln Phe Asp Lys Val Ile His Glu Thr Lys Lys Asp Met Gln
465                 470                 475                 480

Ala Ser Lys Leu Ile Asn Ala Ile Val Gly His Ala Gly Asp Gly Asn
                485                 490                 495

Phe His Ala Phe Ile Val Tyr Arg Thr Pro Glu Glu His Glu Thr Cys
            500                 505                 510

Ser Gln Leu Val Asp Arg Met Val Lys Arg Ala Leu Asn Ala Glu Gly
        515                 520                 525

Thr Cys Thr Gly Glu His Gly Val Gly Ile Gly Lys Arg Glu Tyr Leu
    530                 535                 540

Leu Glu Glu Leu Gly Glu Ala Pro Val Asp Leu Met Arg Lys Ile Lys
545                 550                 555                 560
```

```
Leu Ala Ile Asp Pro Lys Arg Ile Met Asn Pro Asp Lys Ile Phe Lys
            565                 570                 575

Thr Asp Pro Asn Glu Pro Ala Asn Asp Tyr Arg
            580                 585

<210> SEQ ID NO 48
<211> LENGTH: 1764
<212> TYPE: DNA
<213> ORGANISM: S. cerevisiae
<220> FEATURE:
<221> NAME/KEY: gene
<222> LOCATION: (1)..(1764)
<223> OTHER INFORMATION: DLD1 (SGD)

<400> SEQUENCE: 48
atgttgtgga agcgtacttg cacaaggcta ataaagccta ttgcacaacc tagaggaagg      60
ctggtgagaa gatcatgcta cagatacgcc tcaacaggca caggcagcac cgacagcagc     120
agccagtggt taaatactc tgtcatcgcc tcttcagcta ctctattcgg ttatttgttc      180
gctaagaacc tctattctag ggagactaag gaagatttga tagagaagct ggaaatggtc     240
aaaaagatcg acccagtaaa ttctacgtta aagctgtcct cattggactc accagactat     300
ttgcacgacc cggttaagat cgataaggtt gttgaggacc tgaagcaggt gctgggaaac     360
aagcctgaaa actactctga tgcgaaatcc gatttggacg cccattcaga tacctacttc     420
aacacgcatc accccctctcc cgagcaaaga cctaggatta ttattccc tcatactacc      480 gaagaagttt ccaaaatttt gaaaatatgt cacgataaca acatgccagt tgtacccttc     540
tcgggcggaa cgtccttgga ggggcacttc ctgcctacaa gaattggaga taccataacc     600
gtagacctgt ccaagtttat gaataacgtc gtaaaatttg acaagctgga cctggacatc     660
accgtgcagg ccggtctacc ctgggaggat ttgaatgact atttgagcga ccacggtttg     720
atgtttggct gtgaccctgg tccaggtgca cagattggtg ttgcattgc taattcttgt     780 tcaggaacca acgcctaccg ttacggtacc atgaaggaga atattataaa catgactata     840
gtgttgccgg acgggaccat tgtcaagacg aagaaaagac ccagaaagtc gagcgctggc     900
tataacttaa atggtttatt tgtgggaagt gaaggtacct taggtattgt tactgaagct     960
actgtcaagt gtcatgtcaa gcccaaagct gaaactgttg cggtggtatc ctttgatact    1020
atcaaggatg cggccgcatg tgcttctaat ctgactcaga gtggtattca tttgaacgcc    1080
atggagttac tggatgaaaa tatgatgaag ttgatcaacg catctgaatc cacggacaga    1140
tgtgattggg tagagaaacc aactatgttt ttcaagattg gtgggagatc tcccaacatt    1200
gtcaatgctc ttgtggatga agttaaggct gtcgcccagt taaatcactg caacagtttt    1260
cagtttgcta aagatgatga cgaaaaattg gaattatggg aagctagaaa ggtcgcgcta    1320
tggtctgtgc tagacgctga taagagcaaa gacaaatcag ctaaaatttg acaactgat    1380 gtagctgttc ctgtgtcgca gttcgacaag gttattcacg aaactaaaaa ggacatgcaa    1440
gctagtaagc tgatcaacgc cattgttggt catgcaggtg atggtaactt ccatgcattc    1500
atcgtctaca gaacccctga gaacacgaa acctgtagcc aacttgttga cagaatggtc    1560
aagagagcac tgaacgcaga aggcacttgc acgggtgaac acggtgttgg tattggtaaa    1620
agagagtact tgctcgaaga attaggtgaa gcacccgtcg atttgatgag aaagattaag    1680
ctagctattg acccaaagag aatcatgaac ccggacaaaa tctttaaaac tgatccaaac    1740
gagcccgcta atgattacag gtga                                          1764
```

<210> SEQ ID NO 49
<211> LENGTH: 332
<212> TYPE: PRT
<213> ORGANISM: L. plantarum

<400> SEQUENCE: 49

Met Lys Ile Ile Ala Tyr Ala Val Arg Asp Glu Arg Pro Phe Phe
1               5                   10                  15

Asp Thr Trp Met Lys Glu Asn Pro Asp Val Glu Val Lys Leu Val Pro
            20                  25                  30

Glu Leu Leu Thr Glu Asp Asn Val Asp Leu Ala Lys Gly Phe Asp Gly
            35                  40                  45

Ala Asp Val Tyr Gln Gln Lys Asp Tyr Thr Ala Glu Val Leu Asn Lys
        50                  55                  60

Leu Ala Asp Glu Gly Val Lys Asn Ile Ser Leu Arg Asn Val Gly Val
65                  70                  75                  80

Asp Asn Leu Asp Val Pro Thr Val Lys Ala Arg Gly Leu Asn Ile Ser
                85                  90                  95

Asn Val Pro Ala Tyr Ser Pro Asn Ala Ile Ala Glu Leu Ser Val Thr
            100                 105                 110

Gln Leu Met Gln Leu Leu Arg Gln Thr Pro Leu Phe Asn Lys Lys Leu
        115                 120                 125

Ala Lys Gln Asp Phe Arg Trp Ala Pro Asp Ile Ala Lys Glu Leu Asn
    130                 135                 140

Thr Met Thr Val Gly Val Ile Gly Thr Gly Arg Ile Gly Arg Ala Ala
145                 150                 155                 160

Ile Asp Ile Phe Lys Gly Phe Gly Ala Lys Val Ile Gly Tyr Asp Val
                165                 170                 175

Tyr Arg Asn Ala Glu Leu Glu Lys Glu Gly Met Tyr Val Asp Thr Leu
            180                 185                 190

Asp Glu Leu Tyr Ala Gln Ala Asp Val Ile Thr Leu His Val Pro Ala
        195                 200                 205

Leu Lys Asp Asn Tyr His Met Leu Asn Ala Asp Ala Phe Ser Lys Met
    210                 215                 220

Lys Asp Gly Ala Tyr Ile Leu Asn Phe Ala Arg Gly Thr Leu Ile Asp
225                 230                 235                 240

Ser Glu Asp Leu Ile Lys Ala Leu Asp Ser Gly Lys Val Ala Gly Ala
                245                 250                 255

Ala Leu Asp Thr Tyr Glu Tyr Glu Thr Lys Ile Phe Asn Lys Asp Leu
            260                 265                 270

Glu Gly Gln Thr Ile Asp Asp Lys Val Phe Met Asn Leu Phe Asn Arg
        275                 280                 285

Asp Asn Val Leu Ile Thr Pro His Thr Ala Phe Tyr Thr Glu Thr Ala
    290                 295                 300

Val His Asn Met Val His Val Ser Met Asn Ser Asn Lys Gln Phe Ile
305                 310                 315                 320

Glu Thr Gly Lys Ala Asp Thr Gln Val Lys Phe Asp
            325                 330

<210> SEQ ID NO 50
<211> LENGTH: 999
<212> TYPE: DNA
<213> ORGANISM: L. plantarum
<220> FEATURE:
<221> NAME/KEY: gene
<222> LOCATION: (1)..(999)

<223> OTHER INFORMATION: ldhD (Accession no. NC_004567)

<400> SEQUENCE: 50

```
atgaaaatta ttgcatatgc tgtacgtgat gacgaacgtc cattcttcga tacttggatg      60
aaagaaaacc cagatgttga agttaaatta gttccagaat tacttactga agacaacgtt     120
gacttagcta aaggcttcga cggtgccgat gtataccaac aaaaggacta tactgctgaa     180
gtattgaaca agttagccga cgaaggggtt aagaacatct ctcttcgtaa cgttggtgtt     240
gataacttgg acgttcctac tgttaaagca cgtggcttaa acatttctaa cgtacctgca     300
tactcaccaa atgcgattgc tgaattatca gtaacgcaat tgatgcaatt attacgtcaa     360
accccattgt tcaataagaa gttagctaag caagacttcc gttgggcacc agatattgcc     420
aaggaattaa acaccatgac tgttggtgtt atcggtactg gtcggattgg ccgtgctgcc     480
atcgatattt tcaaaggctt cggcgctaag gttatcggtt acgatgttta ccggaatgct     540
gaacttgaaa aggaaggcat gtacgttgac accttggacg aattatacgc ccaagctgat     600
gttatcacgt tacacgttcc tgcattgaag ataactacc acatgttgaa tgcggatgcc     660
ttcagcaaga tgaaagatgg cgcctacatc ttgaactttg ctcgtgggac actcatcgat     720
tcagaagact tgatcaaagc cttagacagt ggcaaagttg ccggtgccgc tcttgatacg     780
tatgaatacg aaactaagat cttcaacaaa gaccttgaag gtcaaacgat tgatgacaag     840
gtcttcatga acttgttcaa ccgcgacaat gttttgatta caccacatac ggctttctac     900
actgaaactg ccgttcacaa catggtgcac gtttcaatga acagtaacaa acaattcatc     960
gaaactggta agctgatac gcaagttaag tttgactaa                             999
```

<210> SEQ ID NO 51
<211> LENGTH: 30
<212> TYPE: PRT
<213> ORGANISM: Artificial Sequence
<220> FEATURE:
<223> OTHER INFORMATION: Mitochondria target sequence of MAE1

<400> SEQUENCE: 51

```
Met Leu Arg Thr Arg Leu Ser Val Ser Val Ala Ala Arg Ser Gln Leu
  1               5                  10                  15
Thr Arg Ser Leu Thr Ala Ser Arg Thr Ala Pro Leu Arg Arg
             20                  25                  30
```

<210> SEQ ID NO 52
<211> LENGTH: 639
<212> TYPE: PRT
<213> ORGANISM: Artificial Sequence
<220> FEATURE:
<223> OTHER INFORMATION: Modified MAE1

<400> SEQUENCE: 52

```
Trp Pro Ile Gln Gln Ser Arg Leu Tyr Ser Ser Asn Thr Arg Ser His
  1               5                  10                  15
Lys Ala Thr Thr Thr Arg Glu Asn Thr Phe Gln Lys Pro Tyr Ser Asp
             20                  25                  30
Glu Glu Val Thr Lys Thr Pro Val Gly Ser Arg Ala Arg Lys Ile Phe
         35                  40                  45
Glu Ala Pro His Pro His Ala Thr Arg Leu Thr Val Glu Gly Ala Ile
     50                  55                  60
Glu Cys Pro Leu Glu Ser Phe Gln Leu Leu Asn Ser Pro Leu Phe Asn
 65                  70                  75                  80
```

```
Lys Gly Ser Ala Phe Thr Gln Glu Glu Arg Glu Ala Phe Asn Leu Glu
                85                  90                  95

Ala Leu Leu Pro Pro Gln Val Asn Thr Leu Asp Glu Gln Leu Glu Arg
            100                 105                 110

Ser Tyr Lys Gln Leu Cys Tyr Leu Lys Thr Pro Leu Ala Lys Asn Asp
        115                 120                 125

Phe Met Thr Ser Leu Arg Val Gln Asn Lys Val Leu Tyr Phe Ala Leu
    130                 135                 140

Ile Arg Arg His Ile Lys Glu Leu Val Pro Ile Ile Tyr Thr Pro Thr
145                 150                 155                 160

Glu Gly Asp Ala Ile Ala Ala Tyr Ser His Arg Phe Arg Lys Pro Glu
                165                 170                 175

Gly Val Phe Leu Asp Ile Thr Glu Pro Asp Ser Ile Glu Cys Arg Leu
            180                 185                 190

Ala Thr Tyr Gly Gly Asp Lys Asp Val Asp Tyr Ile Val Val Ser Asp
        195                 200                 205

Ser Glu Gly Ile Leu Gly Ile Gly Asp Gln Gly Ile Gly Gly Val Arg
    210                 215                 220

Ile Ala Ile Ser Lys Leu Ala Leu Met Thr Leu Cys Gly Gly Ile His
225                 230                 235                 240

Pro Gly Arg Val Leu Pro Val Cys Leu Asp Val Gly Thr Asn Asn Lys
                245                 250                 255

Lys Leu Ala Arg Asp Glu Leu Tyr Met Gly Asn Lys Phe Ser Arg Ile
            260                 265                 270

Arg Gly Lys Gln Tyr Asp Asp Phe Leu Glu Lys Phe Ile Lys Ala Val
        275                 280                 285

Lys Lys Val Tyr Pro Ser Ala Val Leu His Phe Glu Asp Phe Gly Val
    290                 295                 300

Lys Asn Ala Arg Arg Leu Leu Glu Lys Tyr Arg Tyr Glu Leu Pro Ser
305                 310                 315                 320

Phe Asn Asp Asp Ile Gln Gly Thr Gly Ala Val Val Met Ala Ser Leu
                325                 330                 335

Ile Ala Ala Leu Lys His Thr Asn Arg Asp Leu Lys Asp Thr Arg Val
            340                 345                 350

Leu Ile Tyr Gly Ala Gly Ser Ala Gly Leu Gly Ile Ala Asp Gln Ile
        355                 360                 365

Val Asn His Met Val Thr His Gly Val Asp Lys Glu Glu Ala Arg Lys
    370                 375                 380

Lys Ile Phe Leu Met Asp Arg Arg Gly Leu Ile Leu Gln Ser Tyr Glu
385                 390                 395                 400

Ala Asn Ser Thr Pro Ala Gln His Val Tyr Ala Lys Ser Asp Ala Glu
                405                 410                 415

Trp Ala Gly Ile Asn Thr Arg Ser Leu His Asp Val Val Glu Asn Val
            420                 425                 430

Lys Pro Thr Cys Leu Val Gly Cys Ser Thr Gln Ala Gly Ala Phe Thr
        435                 440                 445

Gln Asp Val Val Glu Glu Met His Lys His Asn Pro Arg Pro Ile Ile
    450                 455                 460

Phe Pro Leu Ser Asn Pro Thr Arg Leu His Glu Ala Val Pro Ala Asp
465                 470                 475                 480

Leu Met Lys Trp Thr Asn Asn Asn Ala Leu Val Ala Thr Gly Ser Pro
                485                 490                 495

Phe Pro Pro Val Asp Gly Tyr Arg Ile Ser Glu Asn Asn Asn Cys Tyr
```

-continued

```
                500                  505                  510
Ser Phe Pro Gly Ile Gly Leu Gly Ala Val Leu Ser Arg Ala Thr Thr
        515                  520                  525

Ile Thr Asp Lys Met Ile Ser Ala Ala Val Asp Gln Leu Ala Glu Leu
        530                  535                  540

Ser Pro Leu Arg Glu Gly Asp Ser Arg Pro Gly Leu Leu Pro Gly Leu
545                  550                  555                  560

Asp Thr Ile Thr Asn Thr Ser Ala Arg Leu Ala Thr Ala Val Ile Leu
                565                  570                  575

Gln Ala Leu Glu Glu Gly Thr Ala Arg Ile Glu Gln Glu Gln Val Pro
            580                  585                  590

Gly Gly Ala Pro Gly Glu Thr Val Lys Val Pro Arg Asp Phe Asp Glu
        595                  600                  605

Cys Leu Gln Trp Val Lys Ala Gln Met Trp Glu Pro Val Tyr Arg Pro
        610                  615                  620

Met Ile Lys Val Gln His Asp Pro Ser Val His Thr Asn Gln Leu
625                  630                  635
```